(12) United States Patent
Schewel

(10) Patent No.: US 10,751,180 B2
(45) Date of Patent: Aug. 25, 2020

(54) METHOD AND DEVICE FOR TREATMENT OF VALVE REGURGITATION

(71) Applicant: MTEx Cardio AG, Pfaffikon (CH)

(72) Inventor: Jury Schewel, Hamburg (DE)

(73) Assignee: MTEX Cardio AG, Pfaffikon (CH)

( * ) Notice: Subject to any disclaimer, the term of this patent is extended or adjusted under 35 U.S.C. 154(b) by 0 days.

(21) Appl. No.: 14/901,468

(22) PCT Filed: Jun. 13, 2014

(86) PCT No.: PCT/IB2014/002155
§ 371 (c)(1),
(2) Date: Dec. 28, 2015

(87) PCT Pub. No.: WO2014/207575
PCT Pub. Date: Dec. 31, 2014

(65) Prior Publication Data
US 2016/0302917 A1    Oct. 20, 2016

Related U.S. Application Data

(60) Provisional application No. 61/956,683, filed on Jun. 14, 2013, provisional application No. 61/963,330, (Continued)

(51) Int. Cl.
*A61F 2/24*    (2006.01)
(52) U.S. Cl.
CPC ............ *A61F 2/246* (2013.01); *A61F 2/2412* (2013.01); *A61F 2/2445* (2013.01);
(Continued)

(58) Field of Classification Search
CPC ........ A61F 2/2454–2463; A61F 2/2409–2412; A61F 2220/0008–0016
See application file for complete search history.

(56) References Cited

U.S. PATENT DOCUMENTS

| 5,810,882 A | 9/1998 | Bolduc et al. |
| 6,419,695 B1 | 7/2002 | Gabbay |

(Continued)

FOREIGN PATENT DOCUMENTS

| WO | WO-2014207575 A2 | 12/2014 |
| WO | WO-2014144937 A3 | 4/2015 |

(Continued)

OTHER PUBLICATIONS

International search report and written opinion dated Feb. 5, 2015 for PCT/IB2014/002155.

*Primary Examiner* — Rebecca S Preston
(74) *Attorney, Agent, or Firm* — Wilson Sonsini Goodrich and Rosati, P.C.

(57) ABSTRACT

A prosthetic valve coaptation assist device (100) includes an anchor (101) and a single valve assist leaflet (102). The anchor may be a supporting ring frame, brace or arc structure and will usually be radially self-expandable so that it can expand against surrounding tissue. The valve assist leaflet may be made of pericardium or other biological or artificial material and is shaped like the native target valve leaflet. The valve assist leaflet is typically sized larger than the target leaflet so that after implantation a significant overlap of the device body occurs.

24 Claims, 19 Drawing Sheets

Related U.S. Application Data filed on Dec. 2, 2013, provisional application No. 61/982,307, filed on Apr. 21, 2014.

(52) U.S. Cl.
CPC .......... *A61F 2/2454* (2013.01); *A61F 2/2463* (2013.01); *A61F 2/2466* (2013.01); *A61F 2/2409* (2013.01); *A61F 2210/0014* (2013.01); *A61F 2210/0076* (2013.01); *A61F 2220/005* (2013.01); *A61F 2220/0016* (2013.01); *A61F 2220/0075* (2013.01); *A61F 2230/0006* (2013.01)

(56) References Cited

U.S. PATENT DOCUMENTS

| | | | |
|---|---|---|---|
| 6,478,776 B1 | 11/2002 | Rosenman et al. | |
| 6,663,633 B1 | 12/2003 | Pierson, III | |
| 6,869,444 B2 | 3/2005 | Gabbay | |
| 6,986,775 B2 | 1/2006 | Morales et al. | |
| 7,160,322 B2 | 1/2007 | Gabbay | |
| 7,374,572 B2 | 5/2008 | Gabbay | |
| 7,544,198 B2 | 6/2009 | Parodi | |
| 7,988,725 B2 | 8/2011 | Gross et al. | |
| 8,449,599 B2 | 5/2013 | Chau et al. | |
| 8,870,936 B2 | 10/2014 | Rowe | |
| 9,445,893 B2 | 9/2016 | Vaturi et al. | |
| 9,592,121 B1 | 3/2017 | Khairkhahan | |
| 2001/0021872 A1* | 9/2001 | Bailey .................. | A61F 2/2418 623/1.24 |
| 2005/0004668 A1* | 1/2005 | Aklog .................. | A61F 2/2448 623/2.36 |
| 2005/0010287 A1* | 1/2005 | Macoviak ............ | A61F 2/2445 623/2.36 |
| 2005/0038509 A1 | 2/2005 | Ashe | |
| 2005/0107871 A1* | 5/2005 | Realyvasquez ....... | A61F 2/2454 623/2.11 |
| 2006/0235511 A1* | 10/2006 | Osborne ................ | A61F 2/2412 623/2.12 |
| 2006/0293698 A1 | 12/2006 | Douk | |
| 2011/0319990 A1 | 12/2011 | Macoviak et al. | |
| 2012/0150290 A1 | 6/2012 | Gabbay | |
| 2012/0197388 A1* | 8/2012 | Khairkhahan .......... | A61F 2/246 623/2.11 |
| 2013/0023985 A1* | 1/2013 | Khairkhahan ........ | A61F 2/2466 623/2.38 |
| 2013/0103140 A1* | 4/2013 | Subramanian ........ | A61F 2/2445 623/2.1 |
| 2014/0025163 A1* | 1/2014 | Padala .................. | A61F 2/2412 623/2.18 |
| 2014/0067048 A1* | 3/2014 | Chau ...................... | A61F 2/246 623/2.1 |
| 2014/0350662 A1* | 11/2014 | Vaturi ................... | A61F 2/2412 623/2.1 |
| 2015/0119981 A1* | 4/2015 | Khairkhahan ........ | A61F 2/2442 623/2.36 |
| 2016/0184098 A1 | 6/2016 | Vaturi | |
| 2019/0201192 A1 | 7/2019 | Kruse et al. | |
| 2019/0350705 A1 | 11/2019 | Schewel et al. | |

FOREIGN PATENT DOCUMENTS

| | | |
|---|---|---|
| WO | WO-2016098104 A2 | 6/2016 |
| WO | WO-2018142217 A2 | 8/2018 |

\* cited by examiner

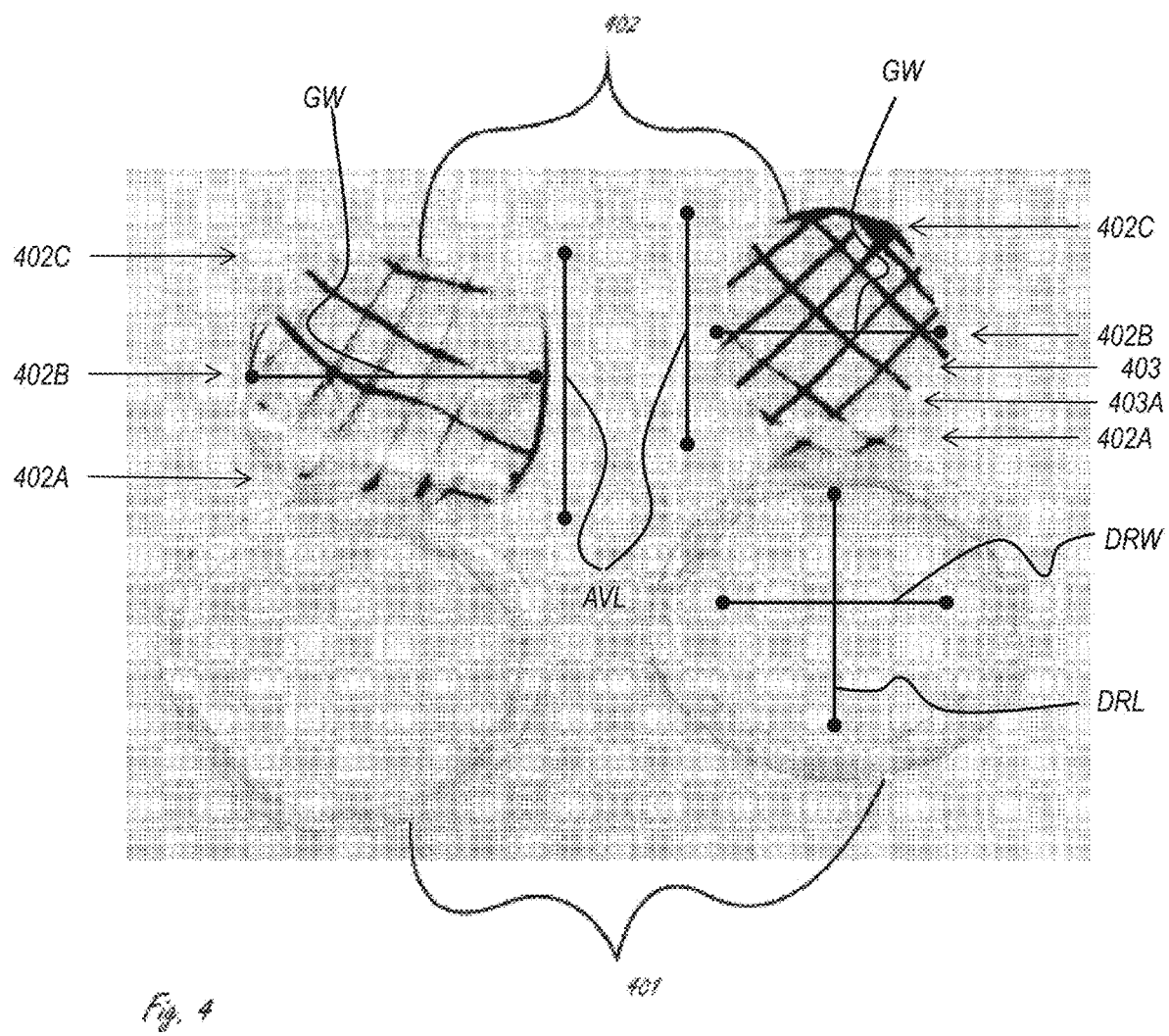

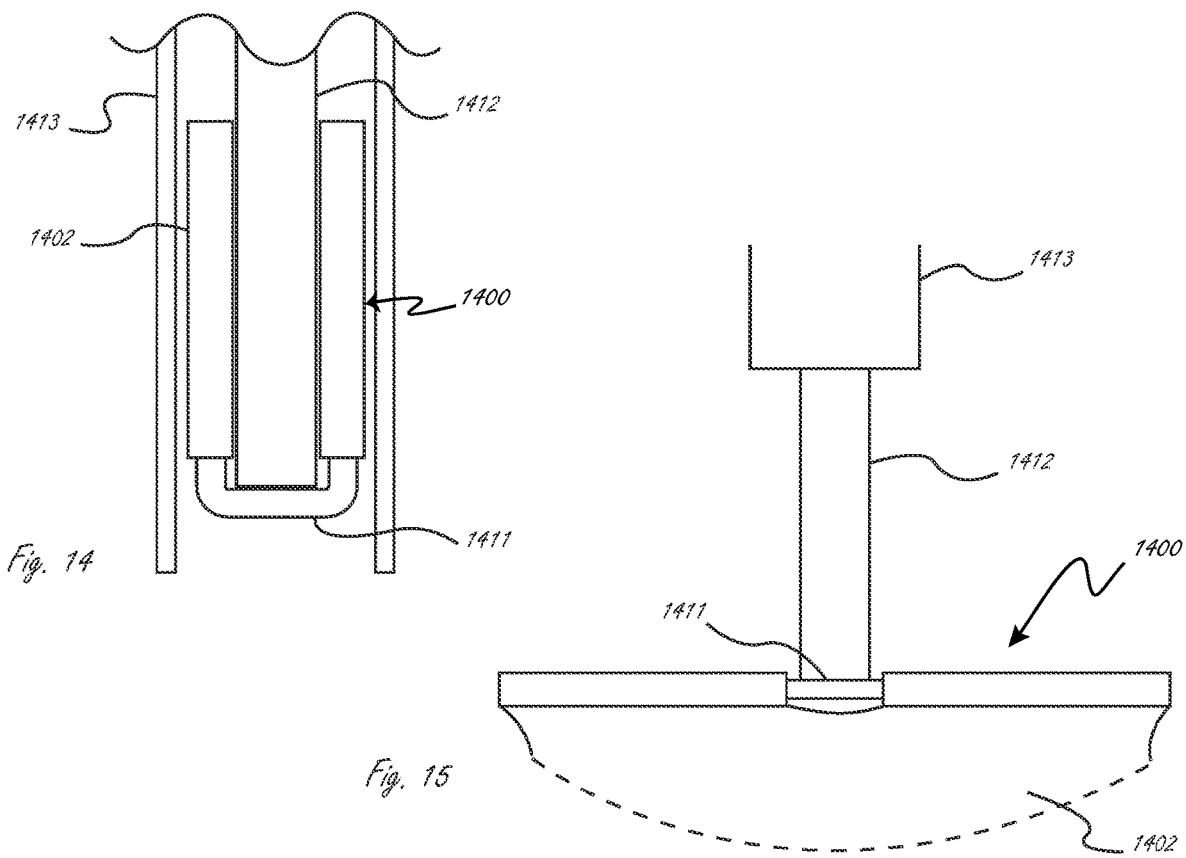
Fig. 14
Fig. 15
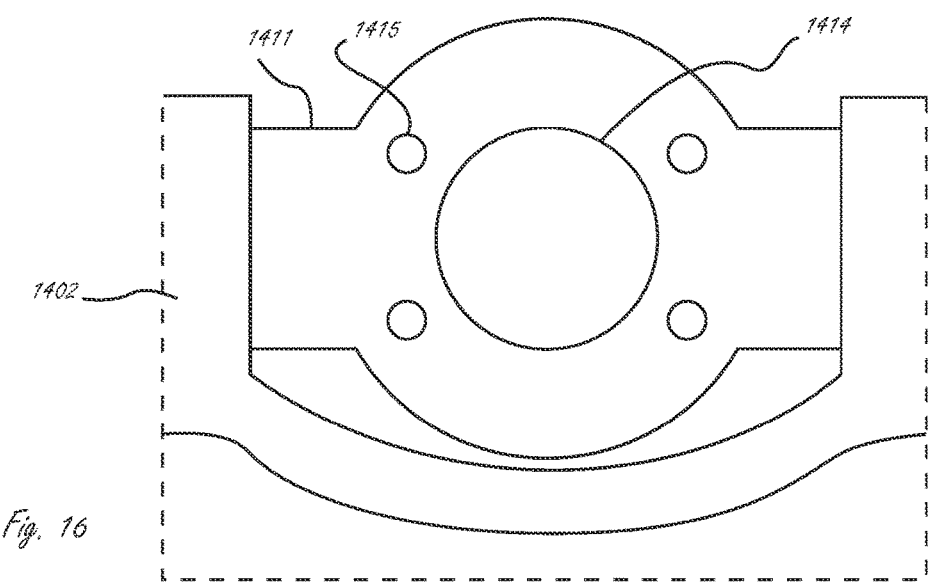
Fig. 16

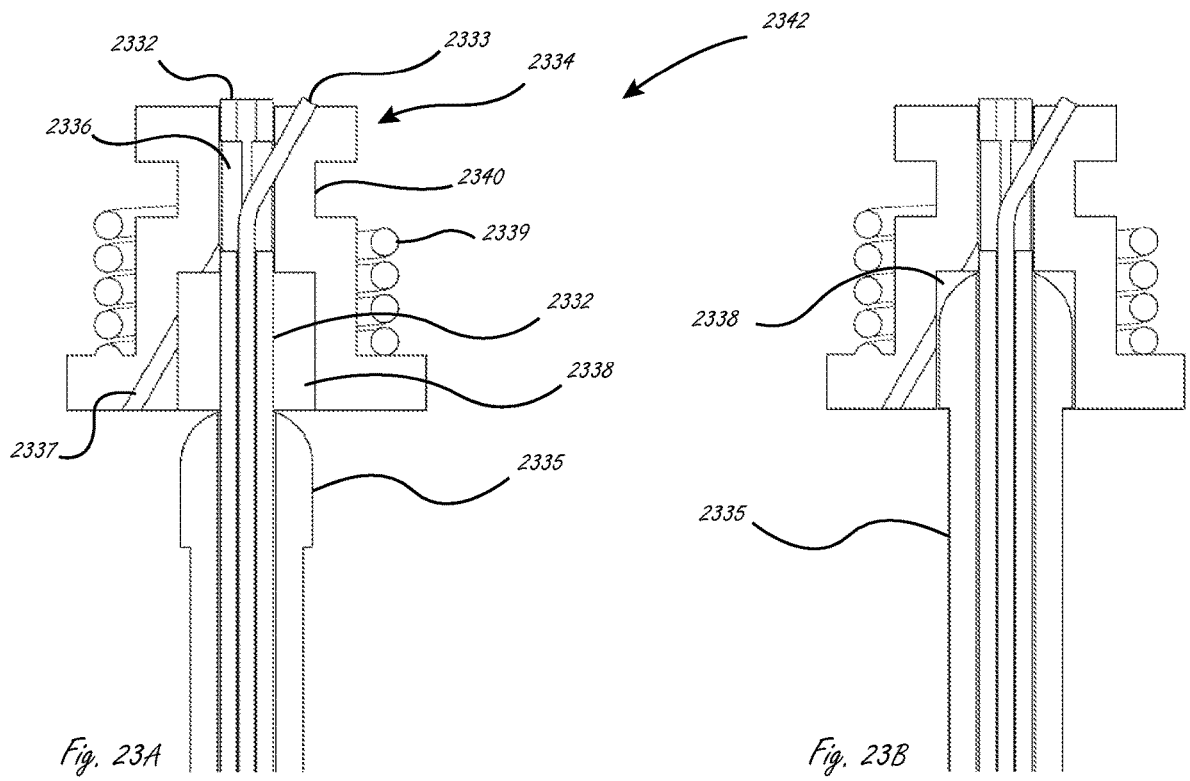
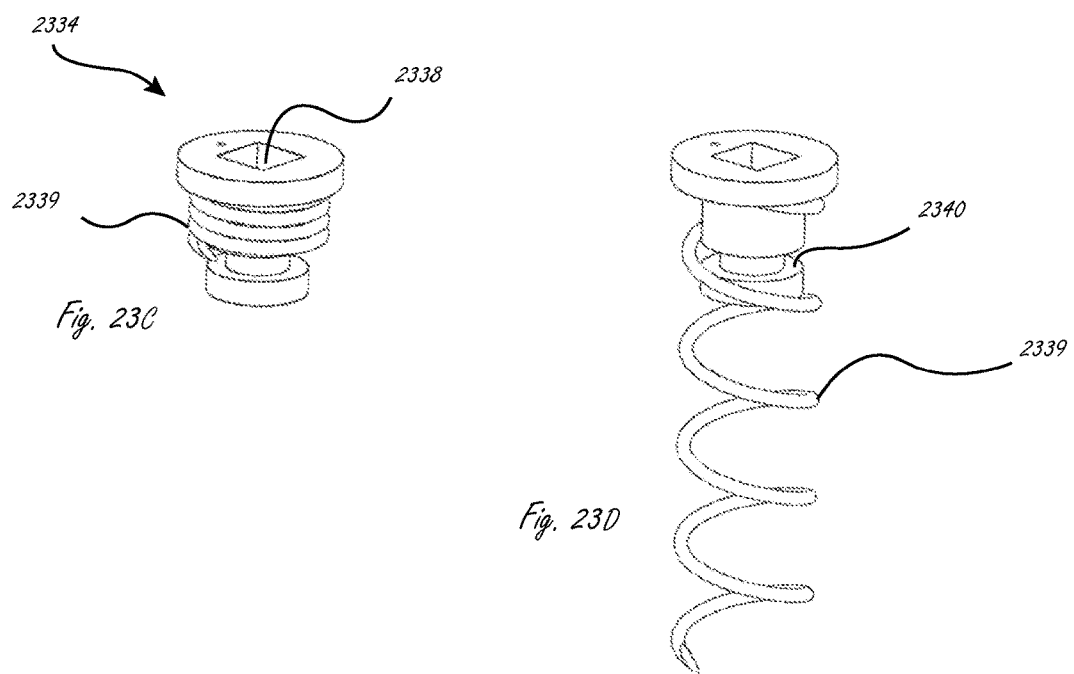
Fig. 23A  Fig. 23B  Fig. 23C  Fig. 23D

METHOD AND DEVICE FOR TREATMENT OF VALVE REGURGITATION

CROSS-REFERENCE TO RELATED APPLICATIONS

This application is a national stage entry of PCT Application No. PCT/IB2014/002155, filed Jun. 13, 2014, which claims the benefit of U.S. Provisional Patent Application Nos. 61/956,683, filed on Jun. 14, 2013; 61/963,330, filed on Dec. 2, 2013; and 61/982,307, filed on Apr. 21, 2014, the full disclosures of which are incorporated herein by reference.

BACKGROUND OF THE INVENTION

1. Field of the Invention

The present invention relates generally to medical devices and methods. More particularly, this invention relates to prosthetic devices and methods for improving the function of prolapsing heart and other circulatory valves.

Mitral valve insufficiency, either organic (primary) or functional (secondary), such as but not limited to prolapsed, regurgitation, and dithering (MVI) is a valvular heart disease characterized by the displacement of an abnormally thickened mitral valve leaflet into the left atrium during systole which can result in poor coaptation of the individual valve leaflets and valve leakage against backpressure. There are various types of MVI, broadly classified as classic and non-classic. In its non-classic form, MVI carries a low risk of complications and often can be kept minimal by dietary attention. In severe cases of classic MVI, complications include mitral regurgitation, infective endocarditis, congestive heart failure, and, in rare circumstances, cardiac arrest, usually resulting in sudden death. The aortic valve can also suffer from prolapse, and valves of the venous circulation can suffer from a similar condition which can lead to chronic venous insufficiency resulting from damaged or "incompetent" valves which are characterized by poor coaptation.

It would be desirable to provide apparatus and methods for improving valve function in a patient suffering from any of the conditions identified above and, in particular, for improving coaptation of cardiac vales, including both mitral valves and aortic valves, as well as venous valves. At least some of these objectives will be met by the inventions described below.

2. Background Art

U.S. Pat. Nos. 6,419,695; 6,869,444; and 7,160,322; and U.S. Patent Publication Nos. 2012/0197388 and 2013/0023985 all have disclosure pertinent to the present invention.

SUMMARY OF THE INVENTION

The description of a prosthetic valve device and implantation method is provided. The present invention generally provides medical devices, systems and methods often used for treatment of mitral valve regurgitation and other valvular diseases including tricuspid regurgitation.

The prosthetic valve device is comprised of a single leaflet sutured to a supporting ring frame, brace or arc structure. The ring frame (referred to henceforth as device ring) is radially self-expandable so that it can expand against the walls of the atrium. The valve device leaflet (referred to henceforth as device body) is made of pericardium or other biological or artificial material and is shaped like the native target valve leaflet. The device body is sized larger than the target leaflet so that after implantation a significant overlap of the device body occurs.

The invention described herein is generally comprised of a percutaneous transcatheter delivery system, a coaptation assisting device and the implantable device body is capable of assuming both a delivery and operational configuration; the delivery configuration being of a small enough size to enable delivery to the implantation site via a percutaneous transcatheter.

The device ring is generally made of metal (e.g. Nitinol), polymer (e.g. polyurethane) or organic substance (e.g. pericardium). At the treatment site the device ring generally is fixed to the annular base of the target valve by anchors which may be part of the device itself or separate from it.

The device body is generally made of synthetic substance (e.g. Dacron or Polyurethane) or organic substance (e.g. pericardium) in some embodiments with an embedded skeleton made of metal, synthetic substance or organic substance, and in some embodiments with a specially designed inferior ledge to prevent systolic prolapsing of the device body.

The device body is generally placed in atrioventricular direction along the blood flow path like the leaflets of the native valve to move back and forth between an open-valve configuration and a closed-valve configuration.

During implantation the device ring should be positioned closely above the ostium of the target valve from the atrial side (e.g. by a transseptal approach). After insertion of the device, the device body leaflet moves within the blood flow synchronously with the target valve leaflet. In the systole after closing of the target valve, the overlap of the device body will be stopped by the edge of the opposing leaflet of the target valve. Thereby the device overlaps the effective regurgitation area (ERO) and minimizes or eliminates the valve regurgitation.

To close or diminish the gap caused by malcoaptation of the native leaflets the device body will be disposed between the native leaflets, thereby providing a surface to coapt against for at least one of the native leaflets, while effectively replacing the function of the second native leaflet in the area of the valve, which it would occlude during systole.

Among other uses, the coaptation assistance device, device body implants and methods described herein may be configured for treating functional and/or degenerative mitral valve regurgitation (MR) by creating an artificial coaptation zone within which at least one of the native mitral valve leaflets can seal. The structures and methods herein will largely be tailored to this application, though alternative embodiments might be configured for use in other valves of the heart and/or body, including the tricuspid valve, valves of the peripheral vasculature, the inferior vena cava, or the like.

In a first specific aspect, the present invention comprises a prosthetic valve coaptation assist device including an anchor configured to be attached to a native valve annulus and a single valve assist leaflet attached to the anchor and configured to lie over a superior surface of a first native valve leaflet when the anchor is attached to the native valve annulus. The single valve assist leaflet is sufficiently flexible so that it will move in unison with the first native valve leaflet and will coapt with a second native valve leaflet in response to blood flow through the valve. In this way, valve prolapse can be reduced and leakage minimized.

In some embodiments of the prosthetic valve coaptation assist device, the anchor is configured to self-expand to attach to the native valve annulus. In other embodiments, the anchor may be configured to be sutured to the native valve annulus. For both self-expanding and sutured anchors, the anchor may be further configured to either fully or partially circumscribe the valve annulus. Anchors which partially circumscribe the valve annulus will frequently have barbs or other tissue-penetrating element which help hold the anchor in place, although barbs may be included on fully circumscribing anchors as well.

The anchors may be formed from metals, polymers, or other biocompatible materials having sufficient strength to remain attached to the valve annulus for indefinite periods after implantation. The valve assist leaflets will typically be formed from flexible materials which may be of the type used in prosthetic heart valves, such as tissues, e.g. pericardium which has been treated to promote stabilization, as well as various synthetic polymers. The valve assist leaflet may also be reinforced with a metal or polymeric a reinforcement structure attached over all or a portion of either or both surfaces of the leaflet.

In a second specific aspect of the present invention, a method for promoting valve coaptation in a patient comprises identifying a prolapsing valve in the patient, e.g. using conventional ultrasonic or other imaging techniques. A single prosthetic valve assist leaflet is implanted over a superior surface of a first native leaflet of the prolapsing valve. The single valve assist leaflet moves in unison with the first native valve leaflet and will coapt with a second native valve leaflet in response to blood flow through the valve. In this way, valve prolapse can be reduced and leakage minimized.

In some embodiments of the methods for promoting valve coaptation of the present invention, the native valve may be a cardiac valve, such a mitral valve or an aortic valve. In other embodiment, the native valve may a venous valve typically a peripheral venous valve.

Implanting may comprise implanting the single prosthetic valve leaflet in an open surgical procedure, but will more typically comprise advancing the single prosthetic valve leaflet endovascularly. transseptally, or transapically, as illustrated in detail below.

When introduced endovascularly. transseptally, or transapically, implanting usually comprises self-expanding an anchor coupled to the single prosthetic valve leaflet within the native valve annulus. The anchor may be expanded to fully circumscribe the valve annulus or may be expanded to partially circumscribe the valve annulus. In both cases, and particularly when the anchor partially circumscribes the annulus, the anchor may include one or more barbs or other tissue penetrating elements which penetrate the native valve annulus as the anchor expands to assist in fixing the anchor to the annulus. Alternatively, in some cases, implanting may comprise suturing an anchor coupled to the single prosthetic valve leaflet to the native valve annulus.

In a third specific aspect of the present invention, a method for delivering a prosthetic valve coaptation assist device to a native valve site comprises providing the prosthetic valve coaptation assist device having an anchor and a single prosthetic valve assist leaflet constrained within a delivery device. The delivery device is advanced to the native valve site, and the prosthetic valve coaptation assist device is deployed from the delivery device at the native valve site. The prosthetic valve coaptation assist device has an anchor which expands within an annulus of the native valve to locate the single prosthetic valve assist leaflet over a superior surface of a native valve leaflet. The single valve assist leaflet moves in unison with the first native valve leaflet and will coapt with a second native valve leaflet in response to blood flow through the valve. In this way, valve prolapse can be reduced and leakage minimized.

In some embodiments of the method for delivering a prosthetic valve coaptation assist devices, the native valve may be a cardiac valve, such a mitral valve or an aortic valve. In other embodiment, the native valve may a venous valve typically a peripheral venous valve.

Advancing may comprise advancing the single prosthetic valve leaflet endovascularly. transseptally, or transapically, as illustrated in detail below.

Deploying will typically comprise releasing prosthetic valve coaptation assist device from constraint so that the anchor self-expands within the native valve annulus to hold the single prosthetic valve leaflet in place over the first native valve leaflet. The anchor may self-expand to fully circumscribe the valve annulus. Alternatively, the anchor may self-expand to partially circumscribe the valve annulus. In eiter case, and particularly in the case of the partial expansion, the anchor may include one or more barbs which penetrate the native valve annulus as the anchor self-expands.

BRIEF DESCRIPTIONS OF THE DRAWINGS

The Figures of the present application use the following reference numbers:

| |
|---|
| (00) leaflet assist device |
| (01) device ring |
| (02) device body |
| (03) posterior mitral leaflet |
| (04) anterior mitral leaflet |
| (05) left ventricle |
| (06) left atrium |
| (07) device leaflet overlap |
| (08) chordae tendineae and papillary muscle |
| (09) inter-atrial septum |
| (10) inter-ventricular septum |
| (11) device strap |
| (12) guiding catheter with anchor system |
| (13) delivery-catheter |
| (14) anchor port |
| (15) 4x orifice for attachment of the guidance catheter |
| (16) guiding catheter of the median anchor system |
| (17) anchor nail |
| (18) guiding catheter of the guiding nail |
| (19) guiding nail |
| (20) guiding catheter with anchor system |
| (21) myocardium |
| (22) median anchor |
| (23) lateral anchors |
| (24) delivery catheter for coupling elements |
| (25) steerable delivery catheter for coupling elements |
| (26) coupler drive element |
| (27) device strap spring element |
| (28) device strap hinge |
| (29) coupling locations |
| (30) perimeter stiffener |
| (31) flexure stiffener |
| (32) guide element sheath |
| (33) guide element lock |
| (34) screw anchor element |
| (35) screw anchor drive |
| (36) guide element sheath slot |
| (37) guide element lock feed-through |
| (38) anchor drive slot |
| (39) helical screw element |
| (40) locking slot |
| (41) steering wire |
| (42) screw anchor system |

FIG. 4 is a photograph of a pair mitral assist device prototypes fabricated from a polymer.

FIGS. 9, 10A, 10B, and 11 illustrate alternative device strap designs.

Figure 12:
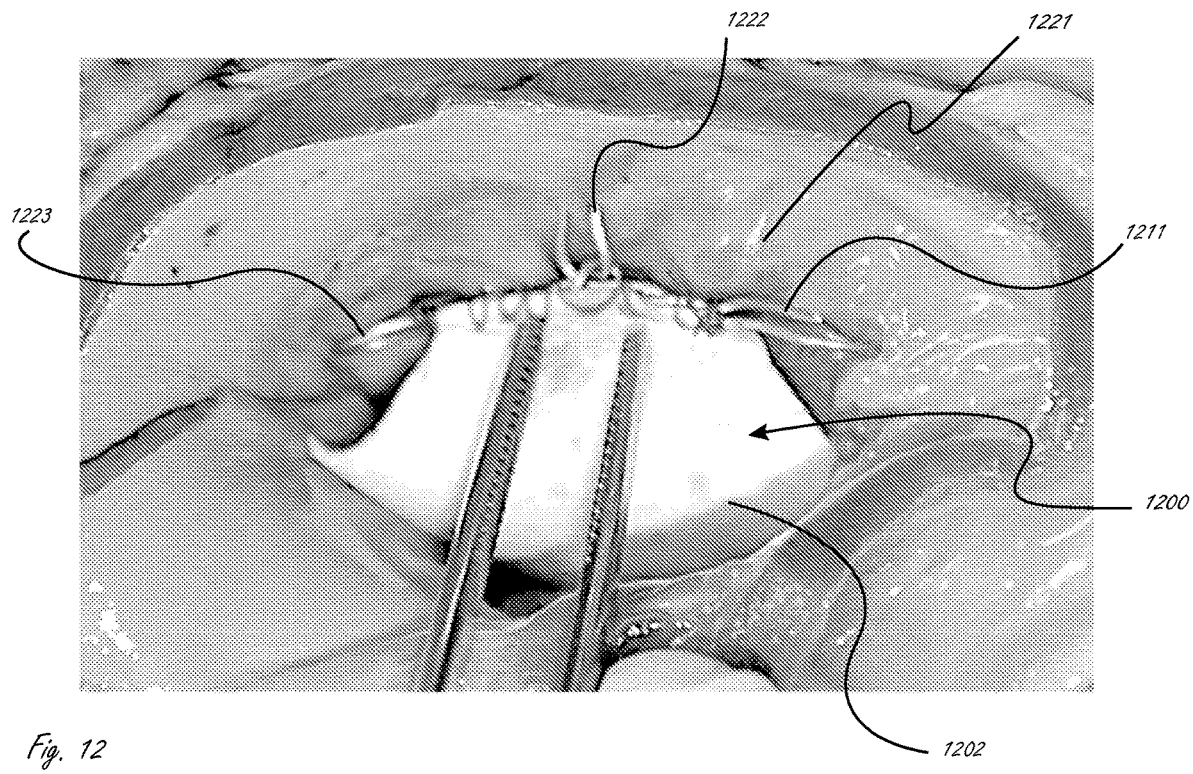

FIG. 12 is a photograph of an alternate mitral assist device viewed from a left atrium after deployment in a pig heart.

Figure 11:
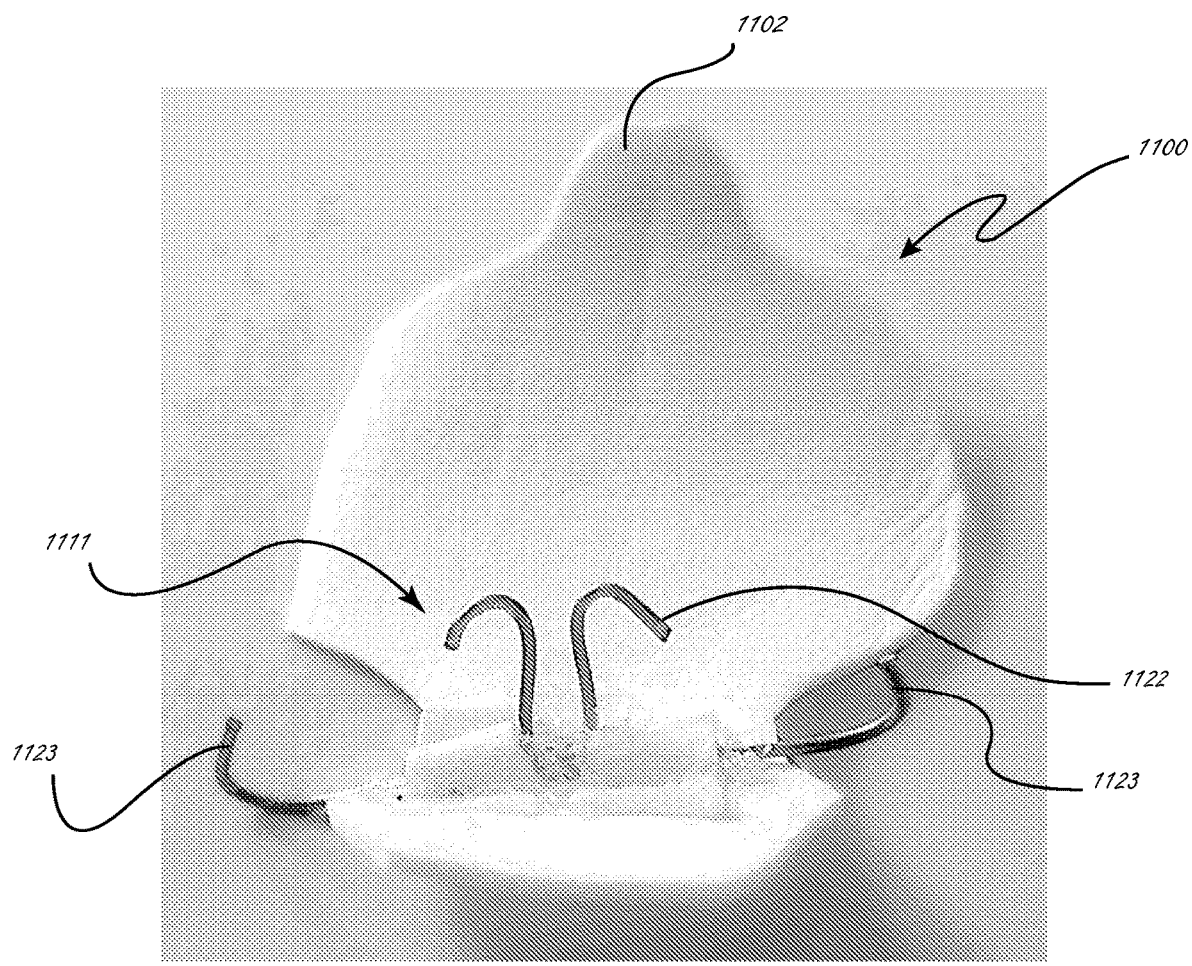
Figure 13:
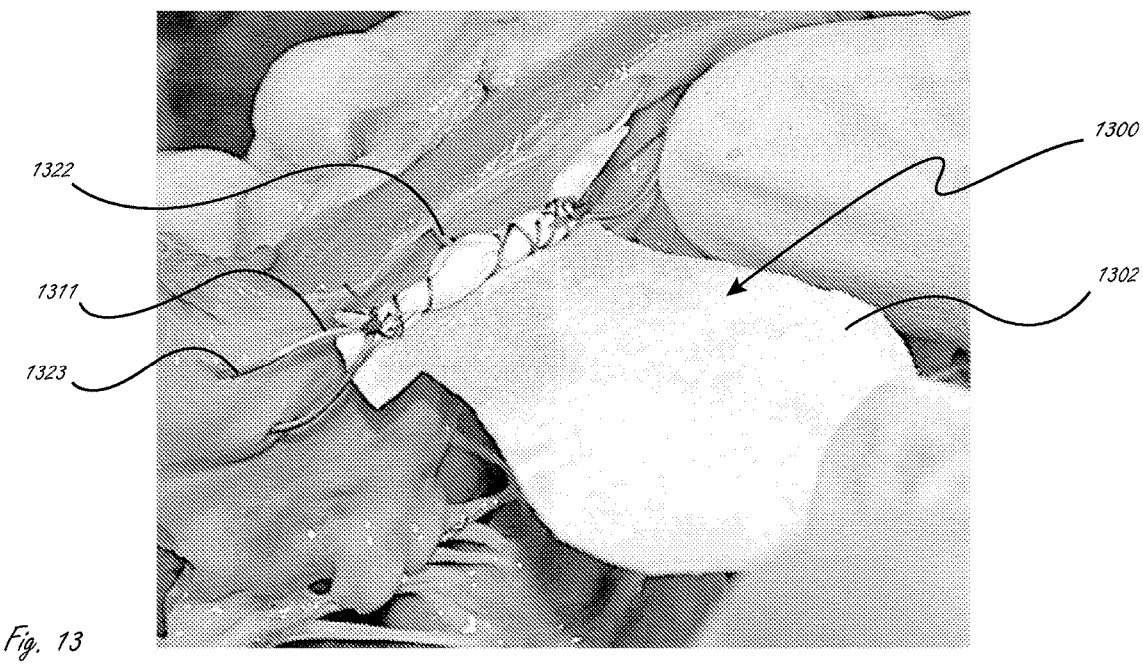

FIG. 13 is a photograph of a further alternative mitral assist device similar to that shown in FIG. 11 shown in a deployed state.

FIGS. 14 through 16 depict aspects of yet another alternative leaflet assist device and deployment system including a guide catheter.

Figure 17A:
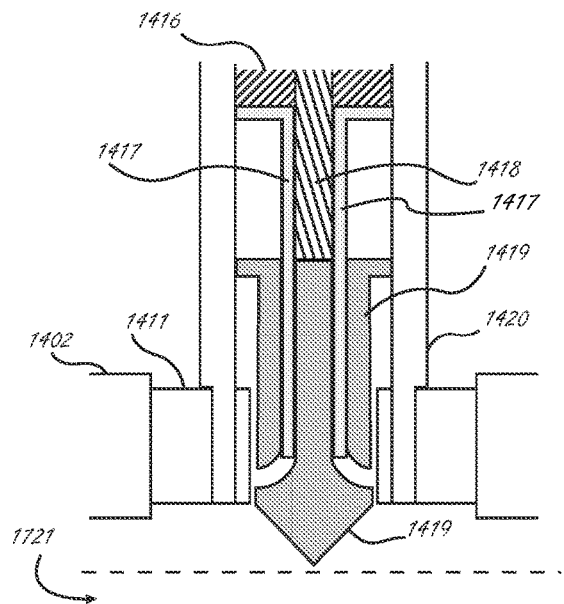

FIG. 17A illustrates a side sectional view of an anchoring portion of the mitral assist device after the assist device has been released from a delivery catheter but prior to activation of the anchor.

Figure 17B:
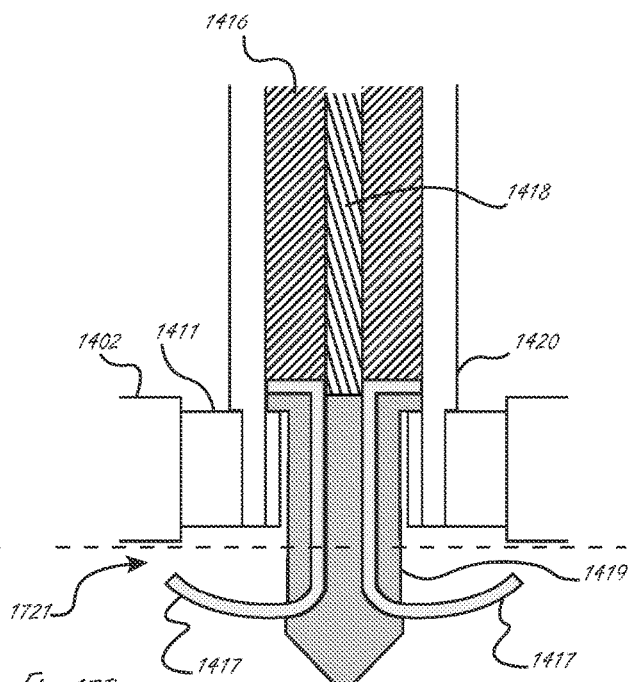

FIG. 17B illustrates the device of FIG. 17A after deployment of the anchor.

Figure 18:
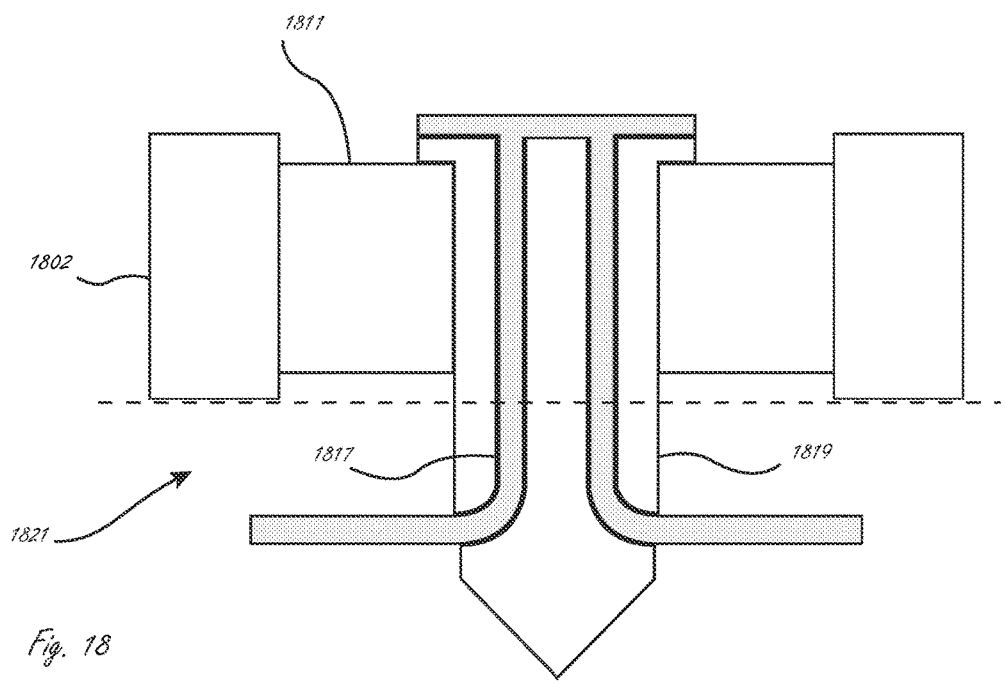

FIG. 18 is a cross-sectional view of an anchoring portion useful with the embodiments of FIGS. 14 through 17A and 17B illustrated in a fully deployed configuration.

FIGS. 19A through 19D illustrate another alternative mitral assist device and delivery system including a delivery catheter visualized at various stages during a delivery cycle.

Figure 19A:
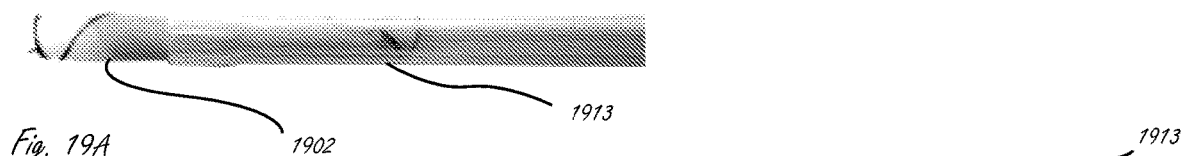
Figure 19B:
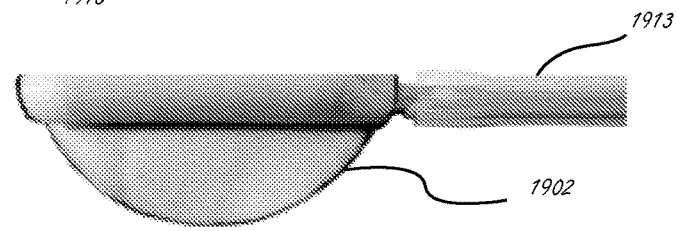
Figure 19C:
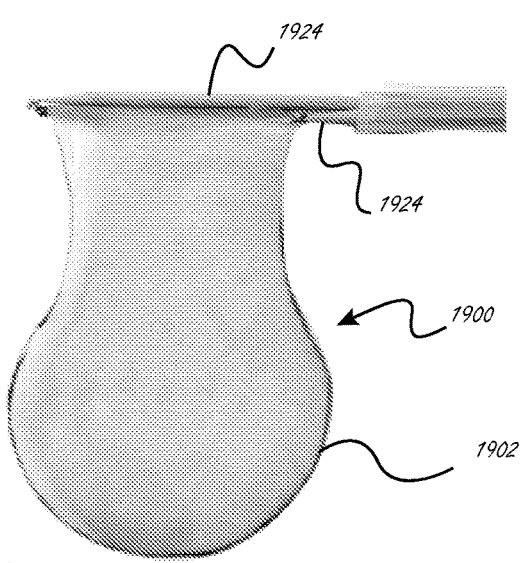
Figure 19D:
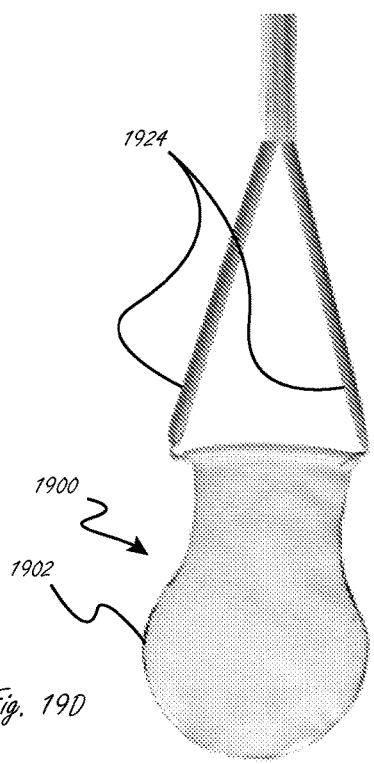
Figure 20:
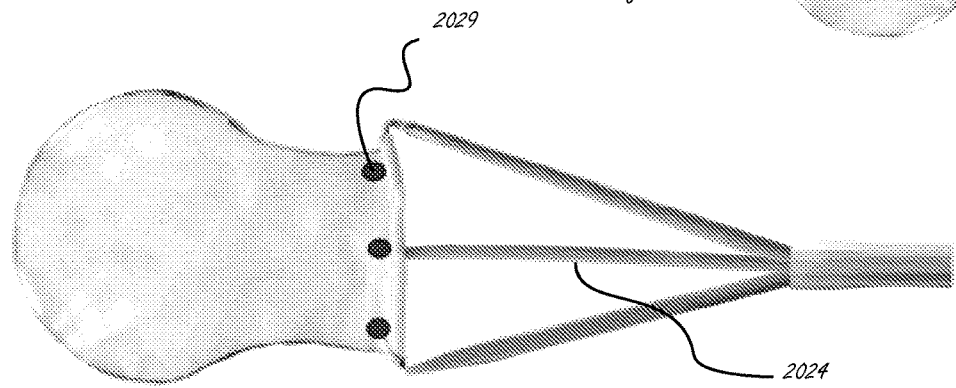

FIG. 20 illustrates a mitral assist device similar to that of FIG. 19 but carried on three coupling delivery catheters.

Figure 21A:
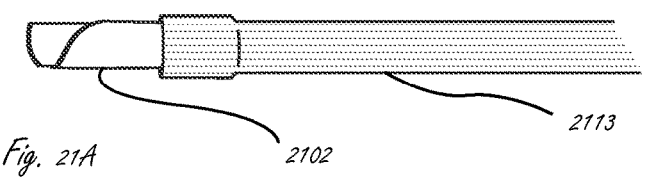
Figure 21B:
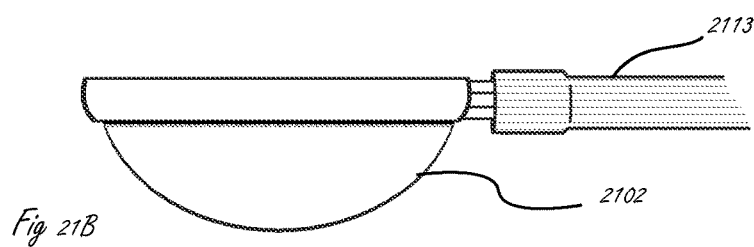

FIGS. 21A though 21D illustrate an alternate embodiment of a coupling element that terminates in an anchoring mechanism which is used to affix the mitral assist device to a myocardium.

Figure 22:
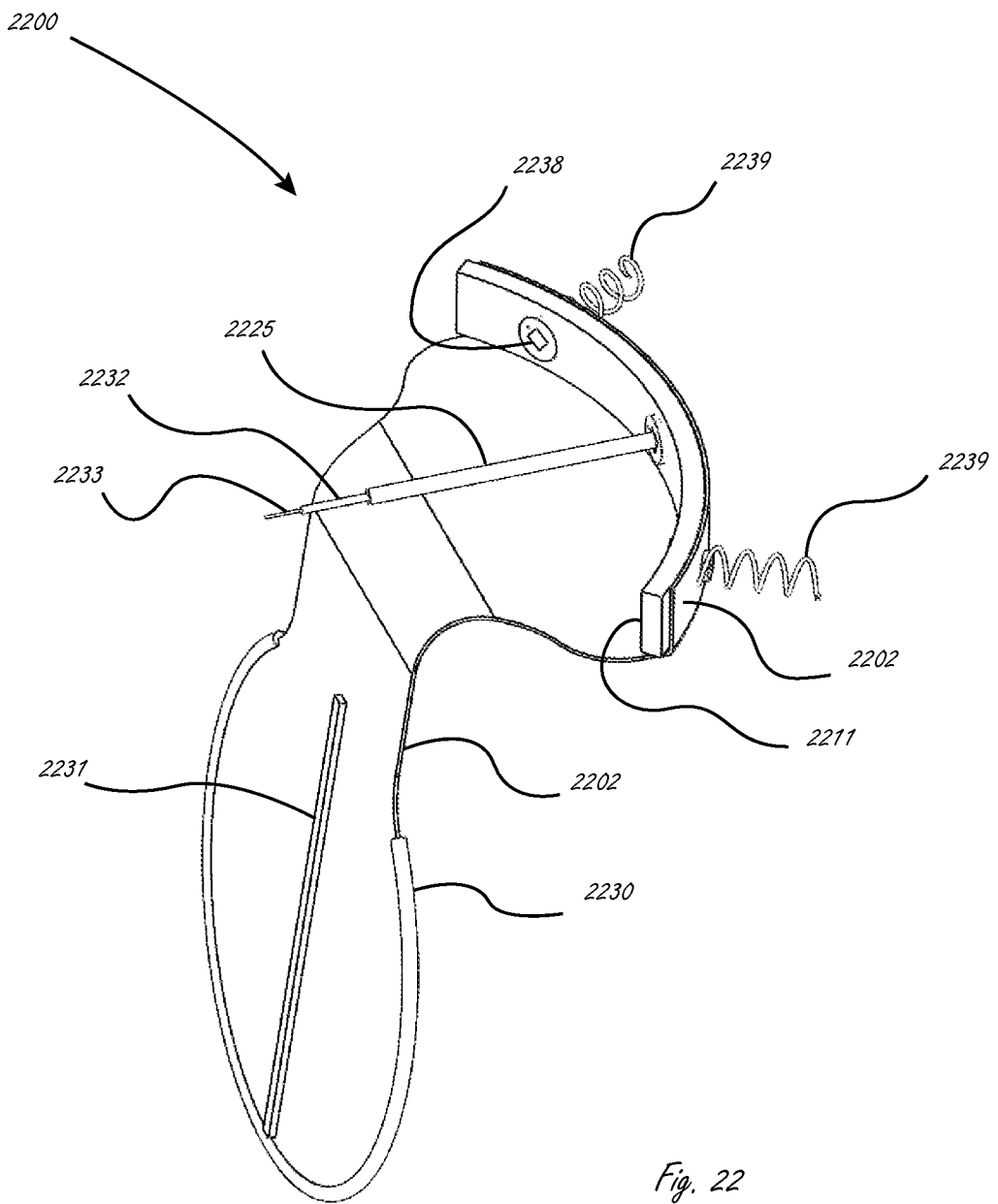

FIG. 22 illustrates a device formed of a molded material having a perimeter stiffener.

FIGS. 23A and 23B show a cross-section of a screw anchor system

FIGS. 23C and 23D illustrate the delivery and operational configurations of screw anchor element of FIGS. 23A and 23B, respectively.

Figure 24:
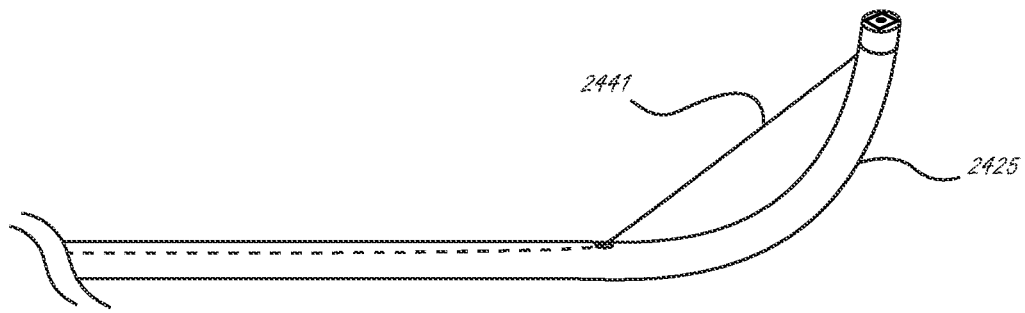

FIG. 24 shows an embodiment of a steerable delivery catheter for coupling elements.

Figure 25:
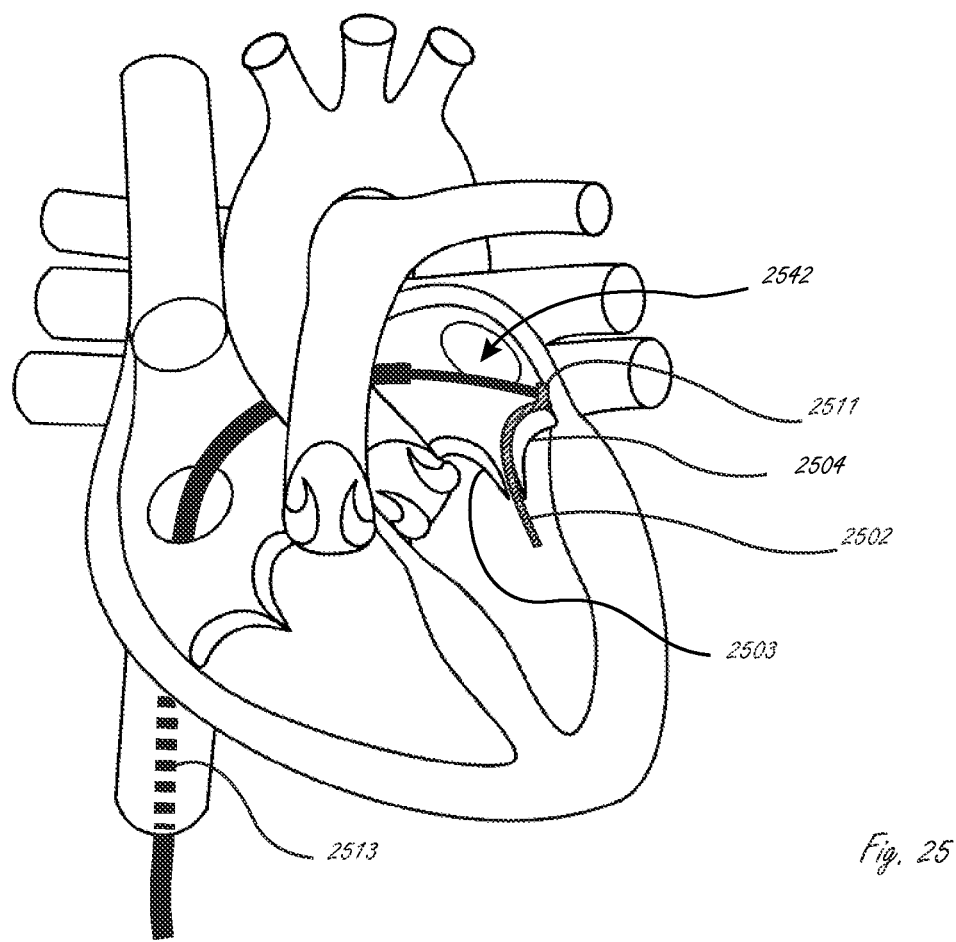

FIG. 25 shows a steerable delivery catheter delivering a device to a target area via an endovascular transseptal approach from an inferior vena cava.

Figure 26:
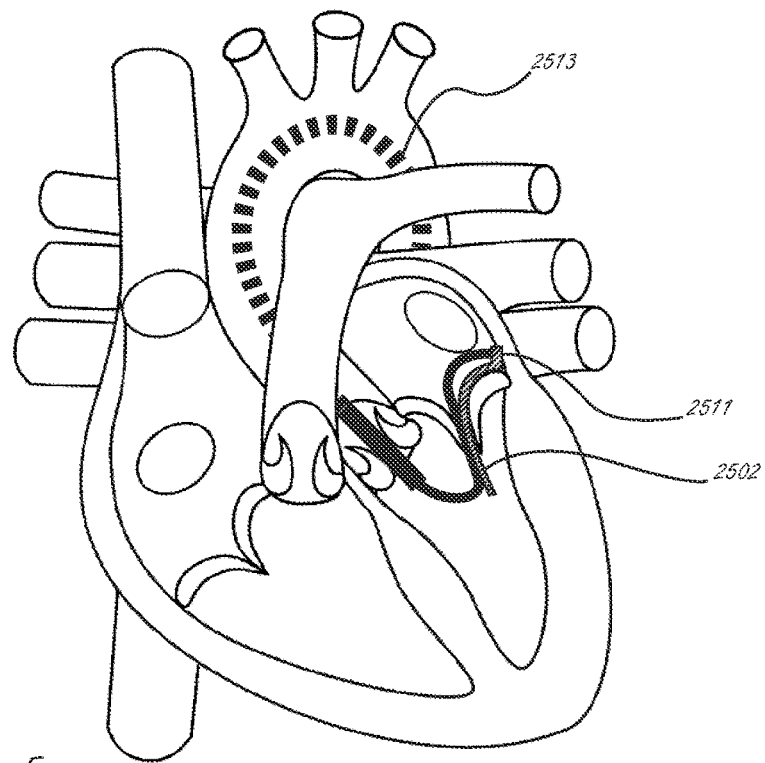

FIG. 26 shows a steerable delivery catheter delivering a device to a target area via an endovascular arterial delivery approach.

Figure 27:
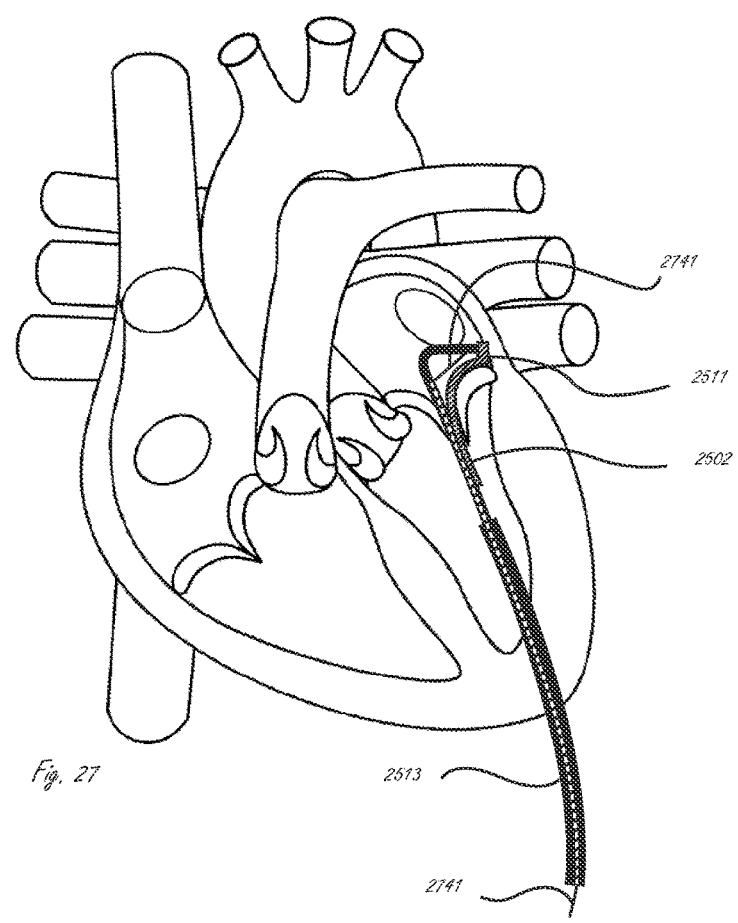

FIG. 27 shows a steerable delivery catheter delivering a device to a target area via a transapical approach.

Figure 28:
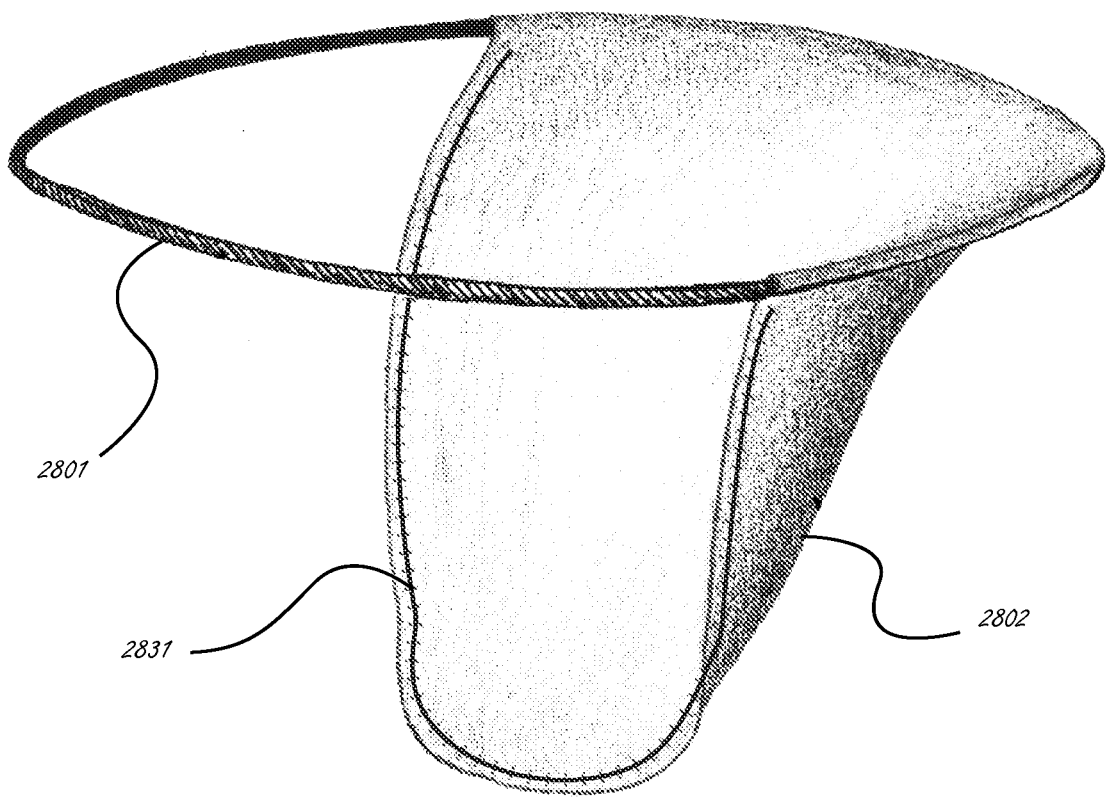

FIG. 28 illustrates a mitral assist device having flexible stiffening present in the perimeter of the mitral assist device body to minimize the upward displacement of the mitral assist device during mitral closure.

DESCRIPTION OF THE INVENTION

Figure 1:
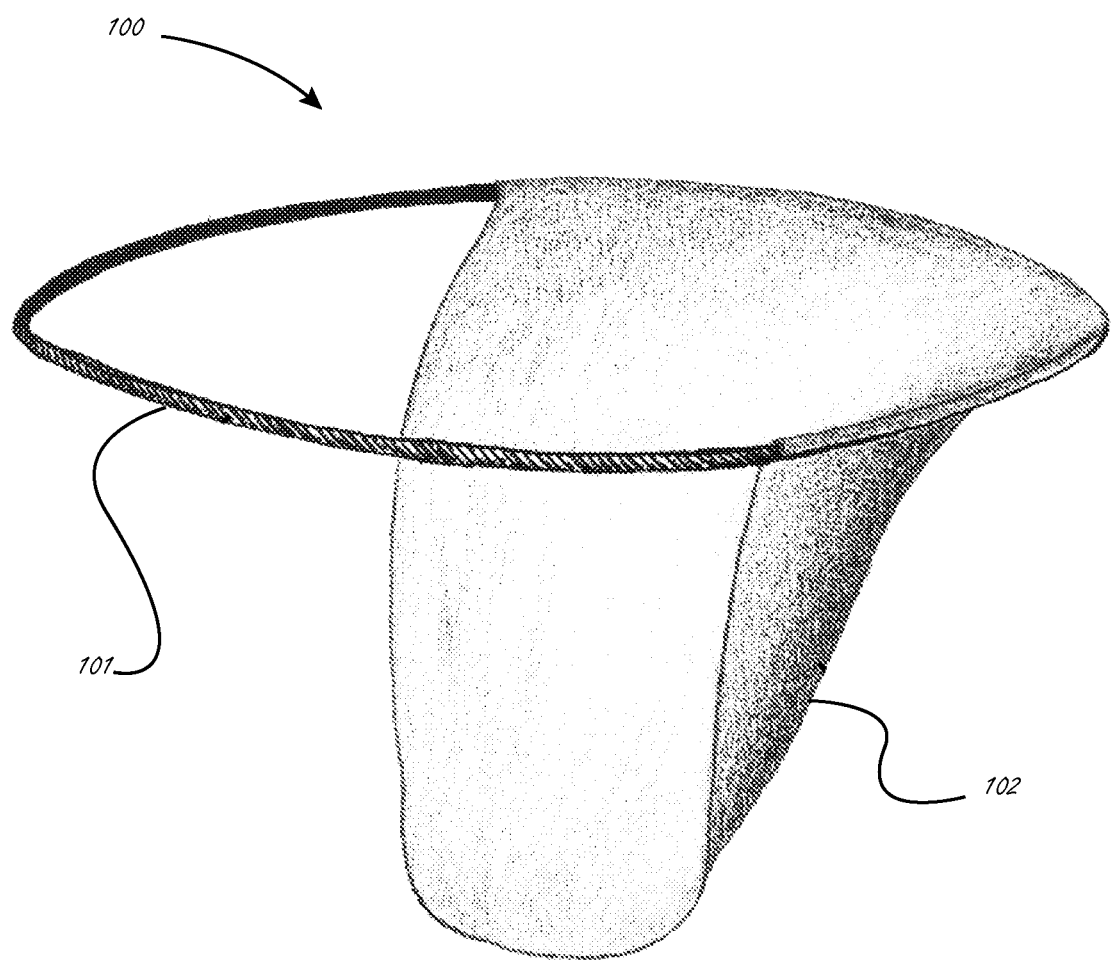
FIG. 1 illustrates a first embodiment of a prosthetic leaflet assist device constructed in accordance with the principles of the present invention.

FIG. 1 depicts a surgically and or percutaneously deliverable prosthetic leaflet assist device 100 having a device ring 101 which serves as an anchor for attaching to tissue near or at the mitral or other valve annulus and a device body or prosthetic leaflet 102 for improving the function of a native (e.g. mitral) leaflet. The leaflet material may be selected from any of the synthetic biocompatible polymers such as Dacron or polyurethane, or treated natural fixed materials such as pericardial or and other material known in the art for use in implantable valves. The device ring is generally made of metal (e.g. Nitinol) or a polymer such as polyurethane. In some embodiments the leaflet is sutured to the ring as when the leaflet is comprised of a natural fixed material. When the leaflet is comprised of a polymeric material it may be sutured, molded, or affixed through the use of adhesive to the device ring. Alternatively the device ring may be threaded through the leaflet. Flexible leaflet 102 interfaces with the native leaflet.

Figure 2A:
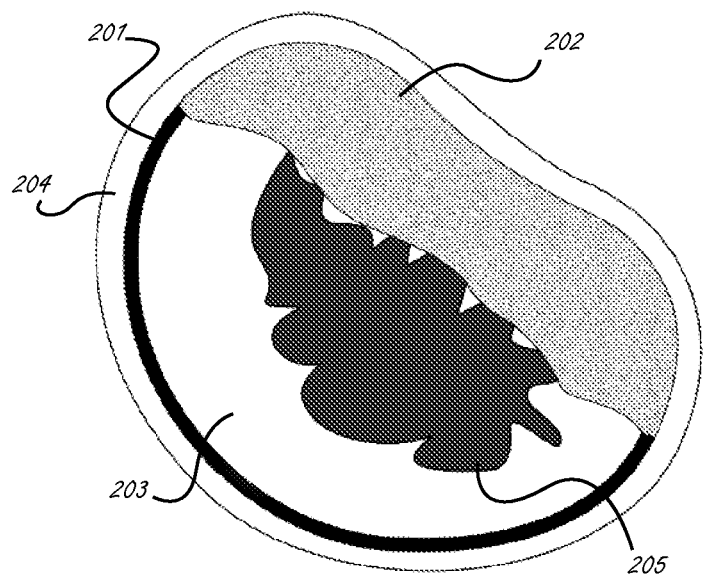
FIGS. 2A and 2B illustrate a prosthetic leaflet assist device implanted in a mitral valve mitral position as viewed from a left atrium during mid-diastole (FIG. 2A) and mid-systole (FIG. 2B).
Figure 2B:
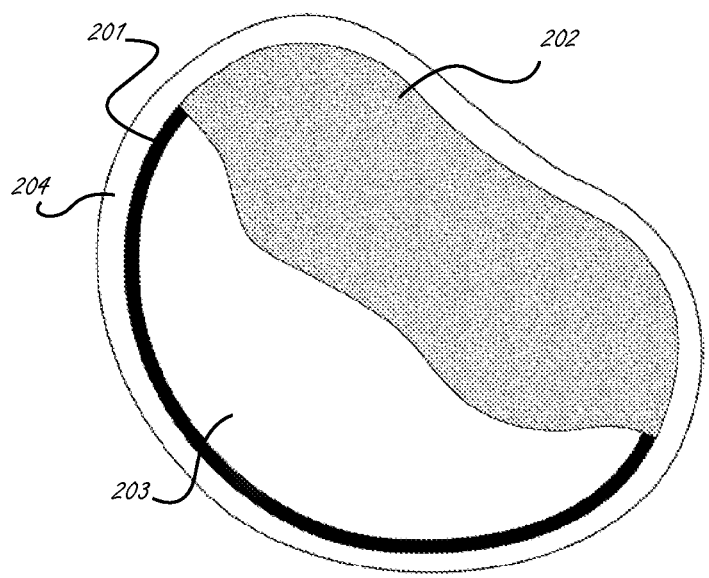

FIG. 2A depicts the device in the mitral position as viewed from a left atrium during mid diastole. The device ring 201 interfaces with the annulus fibrous sinister at the perimeter of the anterior mitral leaflet 204 and the left ventricle 205 can be seen through the open valve. The device leaflet 202 sits opposite the posterior leaflet 203 and over the anterior mitral leaflet 204. FIG. 2B depicts the device during mid systole.

Figure 3:
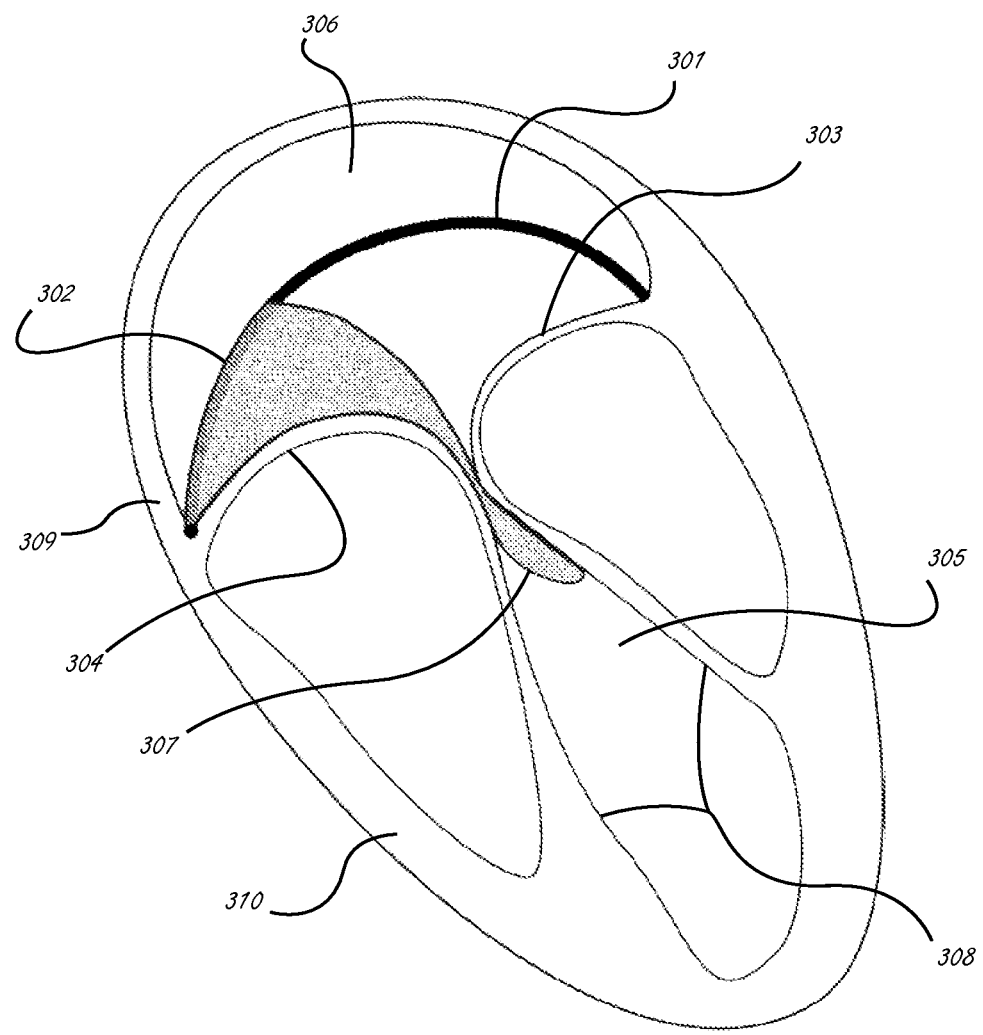
FIG. 3 illustrates the prosthetic leaflet assist device implanted in a mitral valve as viewed from a left atrium during mid-diastole from a side view.

FIG. 3 illustrates the device in mitral valve position during mid diastolic from a side view. Device ring 301 in the left atrium 306 holds the device body or leaflet 302 opposite the posterior mitral leaflet 303 and over the anterior mitral leaflet 304, the leaflet 302 extends into the left ventricle 305 and is captured at overlap 307 between the two mitral leaflets. Chordae tendineae and papillary muscle 308 restrain the natural leaflets. The inter-atrial septum 309 and the inter-ventricular septum 310 are also illustrated.

FIG. 4 shows two mocked up variations of a mitral assist device fabricated of a polymer. As depicted the device bodies 402 are affixed to polymer rings 401. Alternatively the device rings 401 and the device bodies 402 may be molded as a complete device. As illustrated the device bodies are crafted in two different sizes to accommodate different size native mitral valves. As illustrated, the device body 402 may comprise a valve assist leaflet as described herein. The length in an atrioventricular direction AVL may be greater than a greatest width GW of the valve assist leaflet. The length in a device ring DRL may be greater than a greatest length in an atrioventricular direction AVL of the valve assist leaflet. The width in a device ring DRW may be greater than a greatest width GW of the valve assist leaflet. The valve assist leaflet may be lingula or tongue shaped. The valve assist leaflet may be teardrop shaped. The valve assist leaflet may have a first width at the fixed end 402A, a second width between the fixed and ventricular ends in a middle portion 402B greater than the first width, and a third width near the ventricular end 402C less than the second width. The ventricular end 402C may be entirely convex. The valve assist leaflet may have lateral edges 403 that are shaped to have a portion that is concave 403A.

Figure 5A:
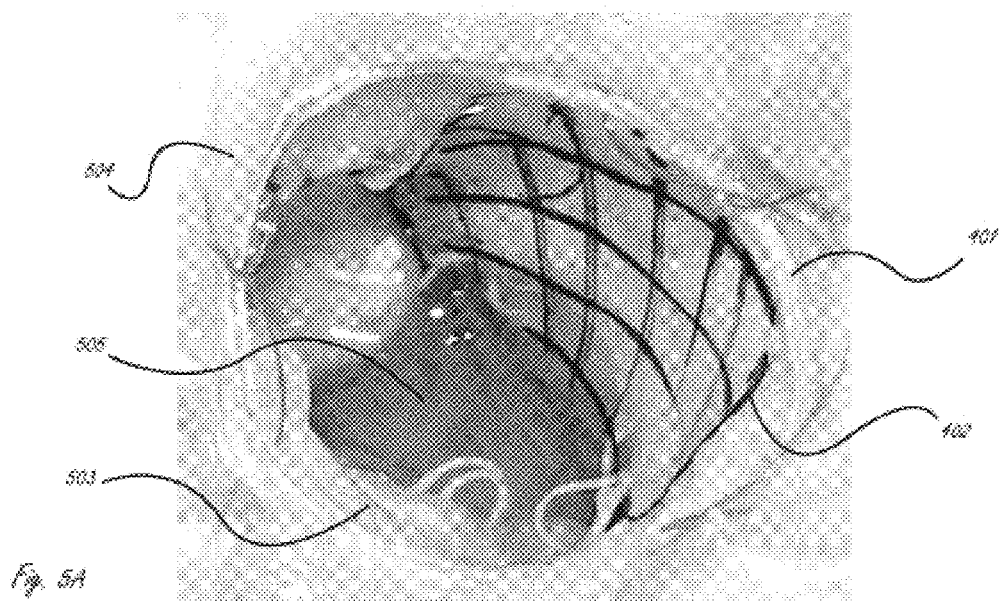
FIGS. 5A and 5B are photographs of a reinforced polymeric prosthetic leaflet assist device taken from the a left pig atrium during simulated mid-systole (FIG. 5A) and mid-diastole (FIG. 5B).
Figure 5B:
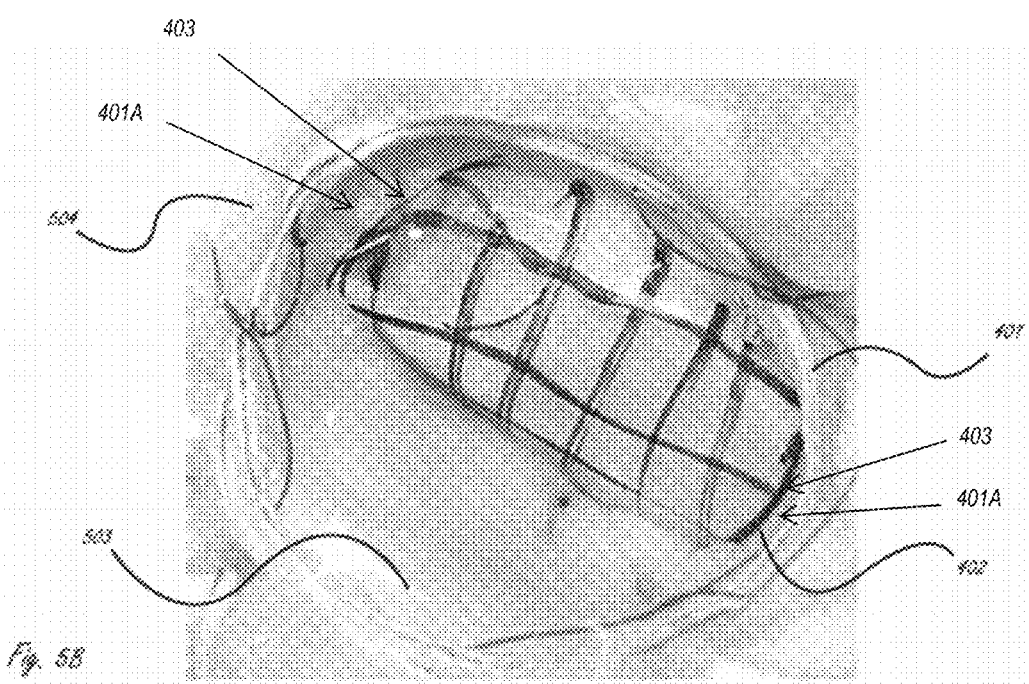

FIG. 5A shows a top view from the left atrium during mid diastole of a mitral assist device comprising device ring 401 and device body 402 sutured into the mitral annulus fibrosus sinister above mitral leaflet 504 of a pig heart. The mitral assist device is oriented such that the device body sits over the anterior mitral leaflet opposite the posterior mitral leaflet 503. The left ventricle 505 is visible through the open valve. FIG. 5B shows the same valve during mid diastole. FIG. 5B further depicts open spaces 401A between the device ring 401 and lateral edges 403 of the valve assist leaflet.

Figure 6A:
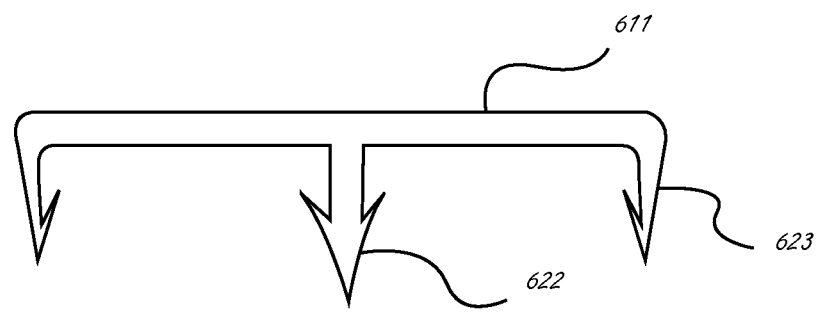
FIG. 6A illustrates a strap for affixing a leaflet assist device to a mitral annulus.
Figure 6B:
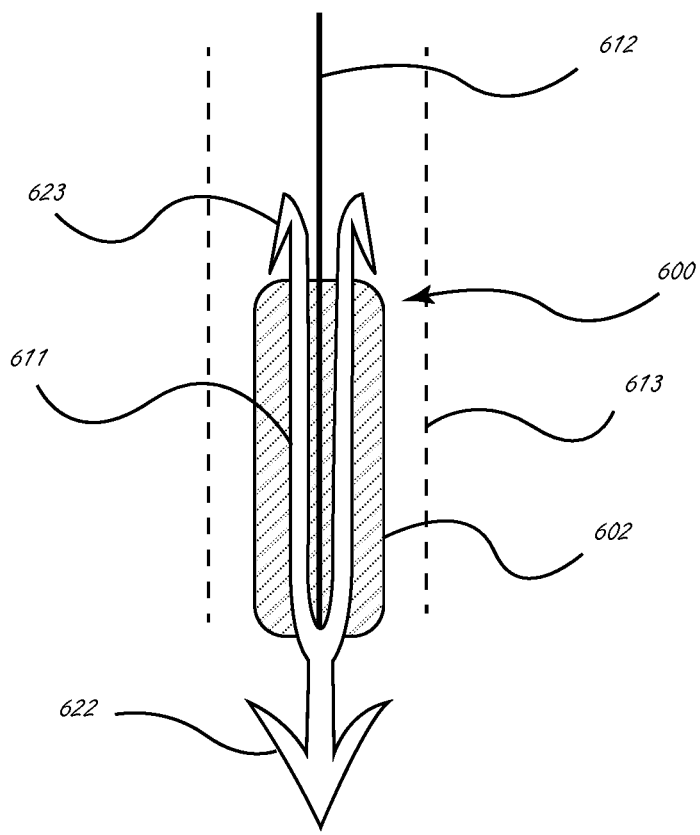
FIG. 6B illustrates the leaflet assist device of FIG. 6A compressed in a catheter for percutaneous delivery.

FIG. 6A illustrates a device strap 611 which provides for an alternate means for affixing a leaflet assist device to the mitral annulus. This arrangement does not require the valve ring to be sutured to the annulus thereby facilitating a simpler percutaneous means of attaching the leaflet assist device. The device strap 611 is comprised of a median or medial anchor 622 and two lateral anchors 623. The anchors are "barbed" structures designed to puncture the heart tissue and lock the device strap in place. FIG. 6B depicts a leaflet assist device 600 configured for percutaneous delivery comprising the anchor strap 611. Device body 602 is wrapped around the device strap 611 which has been folded in half at the median anchor 622. The mitral assist device is constrained in a delivery catheter 613 and at the distal end of a delivery catheter which may be affixed to or separate from the guide catheter 612. When it is affixed a means of detachment is provided for, such as the use of an electrolysible junction as known in the art for the release of arterial stents. The strap is comprised of Nitinol or other material of appropriate resilience. Upon delivery to the atrium the device 600 is pushed from within the delivery catheter 613 with the guiding catheter 612 forcing median anchor 622 into the mitral annulus tissue. The delivery catheter is then moved proximally to release the lateral anchors 623 and valve body 602. As the lateral anchors unfold on release they bury themselves into the annulus tissue.

Figure 7A:
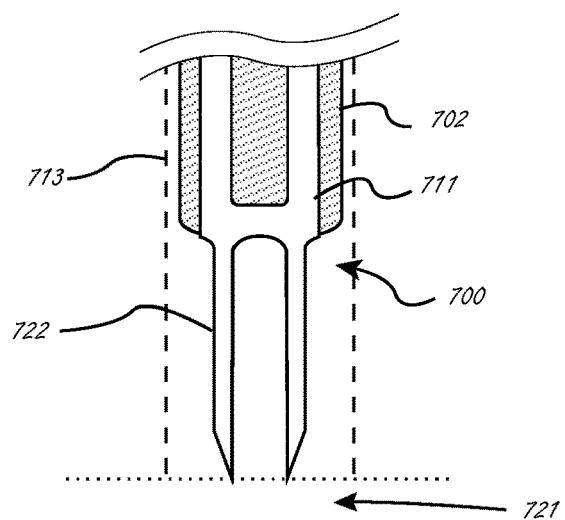
FIG. 7A illustrates a distal portion of a valve assist device configured for delivery within a delivery catheter.
Figure 7B:
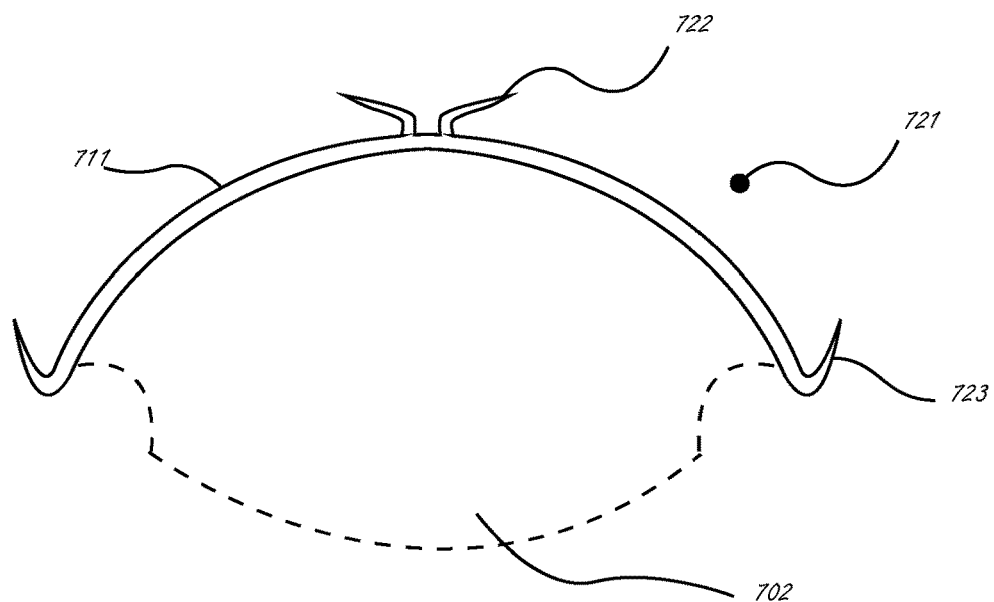
FIG. 7B illustrates the leaflet assist device of FIG. 7A in its deployed configuration.

FIG. 7A illustrates a distal portion of a valve assist device 700 as configured for delivery within a delivery catheter 713. The device strap 713 is bent at its midpoint between the two prongs comprising the median anchor 722 during delivery. As the device is forced into myocardium 721 and released from the delivery catheter 713, the median anchor prongs 722 spread locking the median anchor into the myocardium 721, lateral prongs 723 puncture myocardium. FIG. 7b illustrates the leaflet assist device 700 in its deployed configuration.

Figure 8:
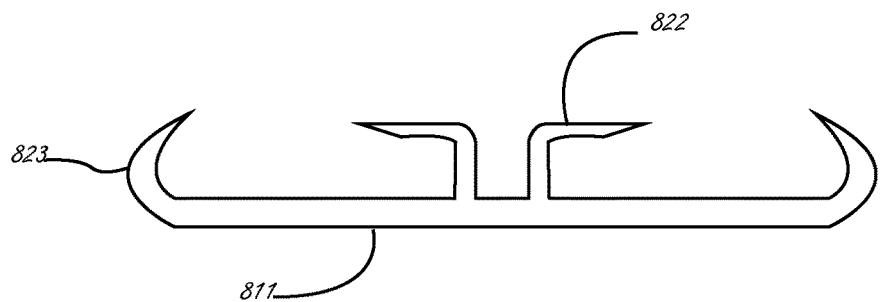
FIG. 8 illustrates a device strap with median anchor elements and lateral anchor elements on an anchor strap.

FIG. 8: Illustrates a version of a device strap wherein median anchor elements 822 and lateral anchor elements 823 are comprised on anchor strap 811. The device strap of FIG. 8 is short enough that it does not require a curved shape to match the annulus.

Figure 9:
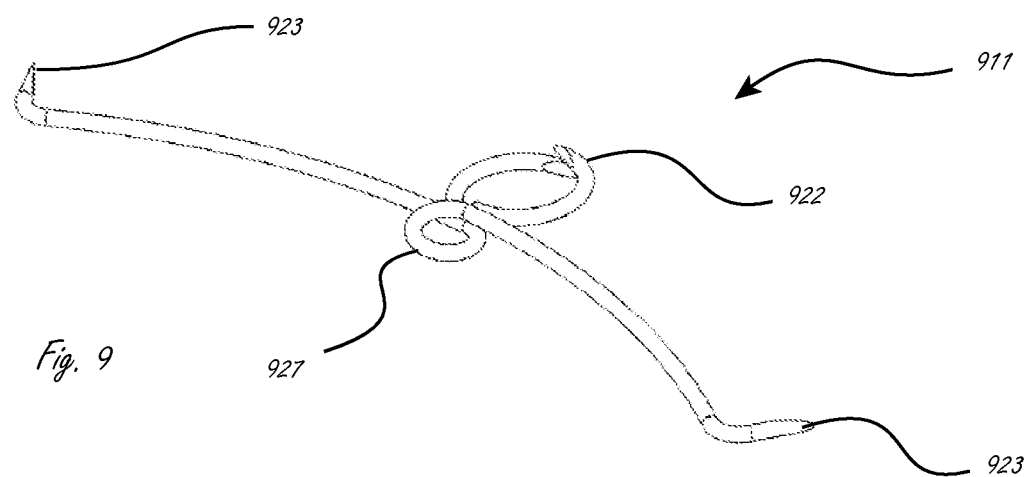

FIGS. 9, 10A, 10B, and 11 represent alternative designs for a device strap. FIG. 9 comprises a device strap fabricated from wire (such as Nitinol or similar material capable of sustaining high strains). Median anchor elements 922 are comprised on the anchor strap 911 on spring element 927. When in a delivery configuration, lateral anchors 923 are pulled together, such that they point away from themselves, and spring element 927 is compressed opening the medial anchor elements. During delivery the open median anchors are pushed against the myocardium and then the delivery catheter is pulled back releasing lateral anchors 923 which, in turn, allows the median anchor elements to close thereby gripping the tissue. Upon release form the delivery catheter lateral anchors 923 additionally swing into a position such that they penetrate into the myocardial tissue.

Figure 10A:
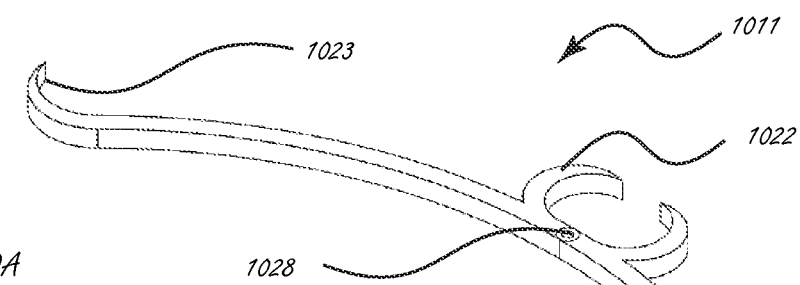
Figure 10B:
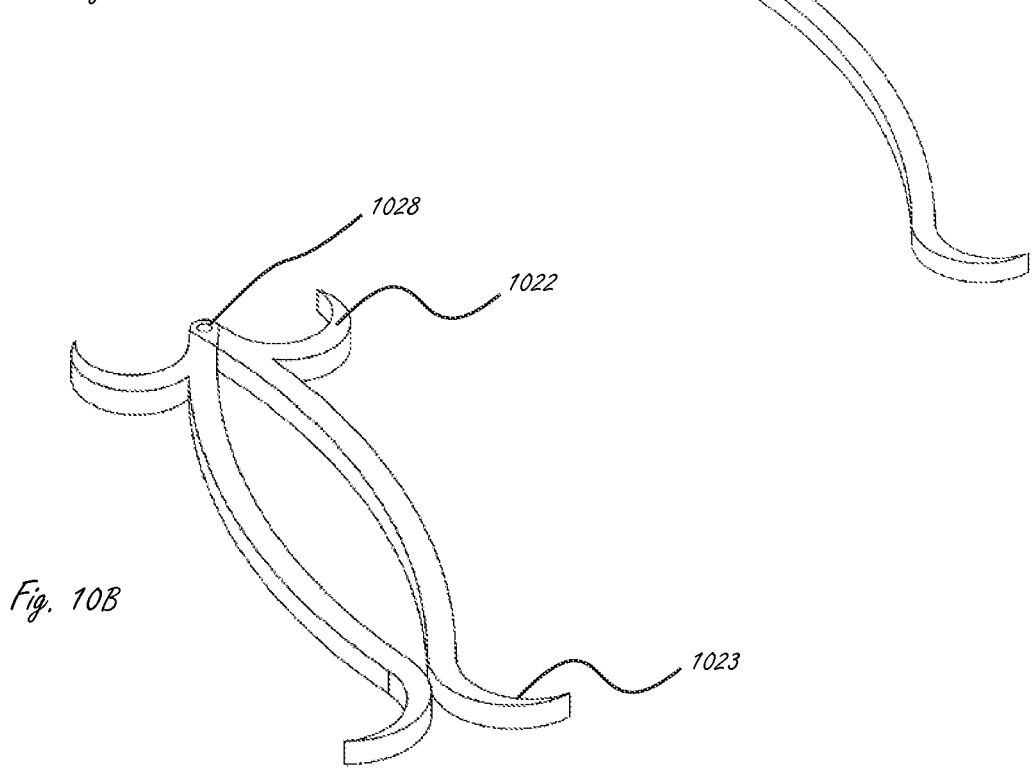

FIGS. 10A and 10B depict an alternate device strap 1011 in a delivered configuration as in FIG. 10A, and a deliverable configuration as in FIG. 10B. The device strap 1011 comprises a hinge element 1028 at the center of the median anchor elements 1022. The hinge element in some embodiments comprises a locking mechanism such that, upon shifting from the deployable configuration of FIG. 10B to the deployed configuration of FIG. 10A, the strap is locked in the deployed configuration with the median anchors locked in a grasping configuration. In some embodiments a spring is used to urge the device strap into a deployed configuration upon release from a delivery catheter. In other embodiments the device strap 1011 is manipulated and locked into the deployed configuration upon release from the delivery catheter.

FIG. 11 is an image of prototypical mitral assist device 1100. The device body 1102 is fabricated from a Dacron felt and the device strap 1111 from a stainless wire. In the image the medial anchors 1122 are bent laterally 90 degrees form their delivery configuration for ease of viewing. The device strap 1111 held in place between layers of Dacron is affixed via glue as shown. In alternate embodiments the layers may be sewn, solvent welded, heat welded, ultrasonically welded, or other suitable means.

In FIG. 12 an alternate mitral assist device 1200 is shown as viewed from a left atrium after deployment. In this embodiment the device strap is comprised of a stainless steel wire similar to that of FIG. 11. In this configuration the lateral anchors are comprised of a pair of anchors on each end of the anchor strap 1211, and a pair of median anchors 1222 directed downward, all of which are hooked into the myocardial tissue 1221. In this embodiment the device body 1202 is affixed to the device strap 1211 by wrapping a portion of the device body around the device strap and locking it in place with suture. The lateral anchors 1223 have been compressed together to minimize their effect on restraining the motion of the impacted myocardial tissue.

In FIG. 13 another alternative mitral assist device similar to that shown in FIG. 11 is shown in the deployed state. The mitral assist device 1300 differs from that of FIG. 12 in that there is only one median anchor 1322 and lateral anchors 1323 have been spread to increase there purchase in the myocardium.

FIGS. 14 through 16 depict aspects of yet another alternative leaflet assist device 1400 and deployment system comprised in a guide catheter 1412. FIG. 14 illustrates the mitral assist device 1400 in a delivery configuration within a delivery catheter 1413 affixed to the distal end of guide catheter 1412 incorporating a delivery system. The valve body 1402 has been pleated to facilitate loading in the delivery catheter 1413. Guide catheter and delivery system 1412 are affixed to the mid section or the device strap 1411. In FIG. 15, is depicted, the mitral assist device 1400 during a deployment after release form the delivery catheter 1413. In FIG. 15 is depicted the device strap 1411 after release from the delivery catheter in its unfolded deployment configurations where the valve body 1402 is unfurled also. The device strap is seen side-on still affixed to the guide catheter and delivery system 1412. FIG. 16 illustrates the central anchoring portion, and anchoring features, of the device strap 1411. This section of the device strap is used during delivery to affix the mitral assist device 1400 to the guide catheter and to anchor the mitral assist device to the myocardium on deployment. The anchor portion of the device strap comprises anchor port 1414, and guide catheter attachment features 1415.

FIG. 17A illustrates a side sectional view of the anchoring portion of the mitral assist device 1400 as configured after the assist device has been released from the delivery catheter and the device body has unfurled, but prior to activation of the anchor. The anchoring portion of the assist device is comprised of the device strap 1411 as described above and an activable anchor mechanism comprised of the following features: a nail guide driver 1418, one or more anchor nails 1417, a nail guide 1419, an anchor nail drive 1416. The section illustrated comprises a section where the anchor nails pass through the guide. These all comprised within the guide catheter 1420 affixed to the device strap 1411 at guide catheter attachment features 1415. As illustrated, the guide catheter has been manipulated to point the mechanism towards the myocardium 1721 at a point near or at the mitral valve annulus. FIG. 17B illustrates the device after deployment of the anchor. Deployment of the anchor after proper alignment as depicted in FIG. 17 is accomplished as follows. Anchor guide nail driver 1418 and anchor nail drive 1416 are simultaneously pushed out of the guide catheter 1420 into the myocardial tissue until the guide nail 1419 has seated against the device strap 1411. Anchor nail driver 1416 is then pushed distally forcing the anchor nail forward through the nail guide 1419 and into the myocardium. The anchor nail is deformed as it passes through the nail guide thereby locking the anchor nail in the myocardial tissue.

A cross section of the anchoring portion of an embodiment similar to that of FIGS. 14 through 17A and 17B is illustrated in its fully deployed configuration in FIG. 18. In this embodiment only one driver is required to actuate both the guide nail and the anchor nail. The mechanism relies on the increased force required to actuate the anchor nail vs. the penetrating the myocardium with the anchor assembly. During deployment the anchor assembly, comprised of the nail guide 1819 and the anchor nail 1817, is pushed into the myocardium until the anchor assembly seats itself against the top surface of the of the device strap 1811. At this point the anchor nail prongs are straight and are contained within the straight portions of the nail guide. Upon seating, and therefore penetrating the myocardium, the force of actuation is increased and the anchor nail 1817 is pushed through the nail guide thereby deforming the distal ends of the anchor nail as shown in FIG. 18. The cross section shown in FIG. 18 is rotated off of the cross section incorporating the attachment locations for the delivery catheter.

FIGS. 19A through 19D illustrate another alternative mitral assist device and delivery system comprised in a delivery catheter visualized at various stages during a delivery cycle. FIG. 19A illustrates the distal end of the delivery system with the mitral assist device body 1902 rolled around a set of delivery coupling elements (not visible), partially pushed out of the delivery catheter 1913. In FIG. 19B the mitral assist device body 1902 has been completely pushed out of the delivery catheter 1913 and partially unrolled. In FIG. 19C the mitral assist device 1900 illustrated is completely unrolled and tethered to coupling elements 1924. The mitral assist device 1900 is oriented at 90 degrees to the delivery catheter at this time and delivery coupling elements 1924 are visible. In FIG. 19D the mitral assist device 1900 has been rotated by 90 degrees by withdrawing the delivery catheter relative to the mitral assist device or pushing the coupling elements further out of the delivery catheter and then equalizing the length of the coupling elements delivered from the delivery catheter. In this fashion the orientation of the mitral assist device may be adjusted through a range of angles to better facilitate alignment with the mitral valve annulus prior to affixing it in place.

FIG. 20 illustrates a mitral assist device similar to that of FIG. 19 but carried on three coupling delivery catheters 2024; the device is then affixed in place via anchoring elements at anchor locations 2029 using an anchor installation tool (not shown).

The device of FIGS. 19 and 20 may be affixed in place by a number of different means. These include but are not limited to any of the following. The device may be placed appropriately within the mitral valve followed by placement of a mitral annuloplasty band (not shown). The annuloplasty band is then affixed in place locking the mitral assist device between the annuloplasty band and the mitral wall. One such band useable in this fashion is the Valtech Cardioband. Alternatively, anchoring elements may be delivered via a second delivery catheter and used to anchor an attachment edge of the mitral assist device to the myocardium. Anchor elements may be but are not limited to any of the following configurations: helical anchors as described by Rosenman U.S. Pat. No. 6,478,776 but including a cap; helical anchors as described by Gross U.S. Pat. No. 7,988,725; expandable nail anchors as described herein; staple anchors as described by Morales U.S. Pat. No. 6,986,775.

Figure 21C:
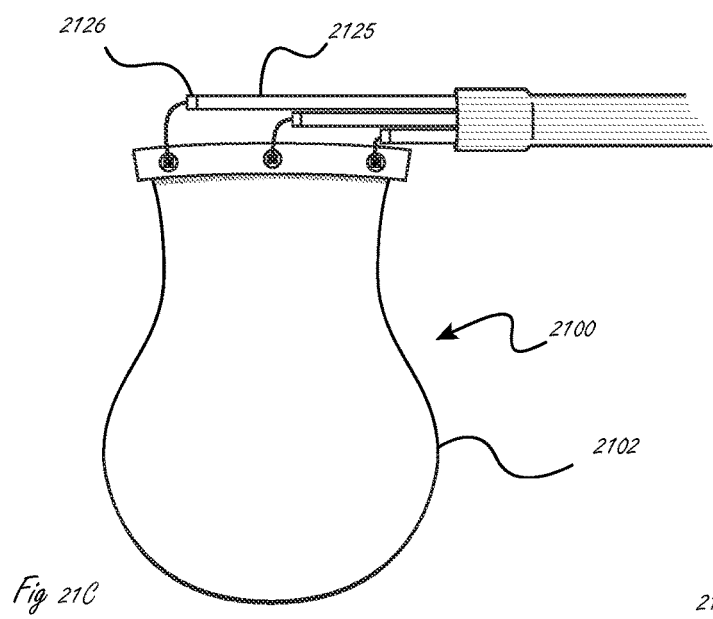
Figure 21D:
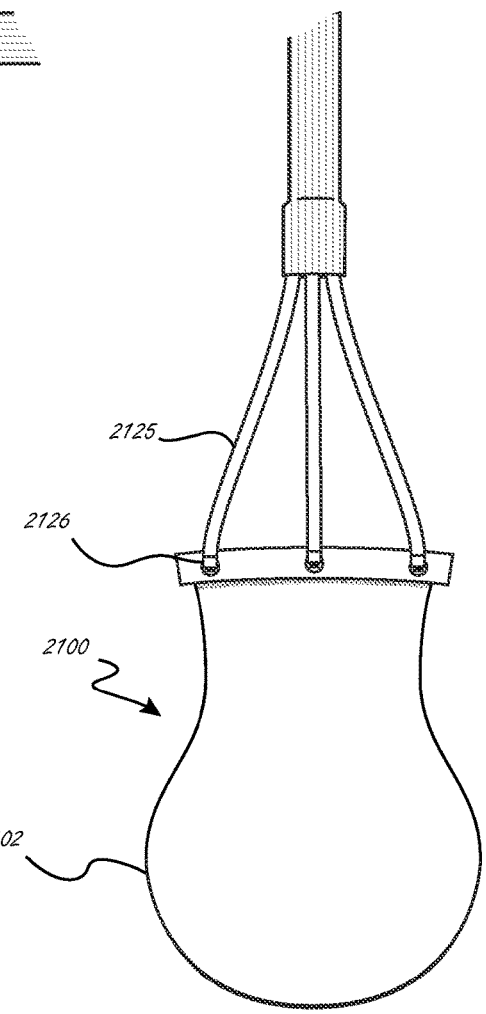

In an alternate embodiment the coupling elements may be terminated in an anchoring mechanism, which is then used to affix the mitral assist device to the myocardium. FIG. 21 illustrates such a device. FIG. 21C is illustrated after the mitral assist device 2100 has been delivered from within the delivery catheter 2113, the device body has been unfurled, and the steerable coupling elements 2130 have been manipulated to a plane parallel to the longitudinal axis of the delivery catheter. During a deployment the device coupling locations would be aligned with or near the mitral annulus, and steered such that they were face-on to the myocardium. In such a configuration the terminal anchoring mechanism may comprise any of the anchoring means previously described herein.

When the device body is comprised of a molded material as shown in FIG. 22, the perimeter stiffener 2230 may be molded in the device body 2202. In addition to a perimeter stiffener 2230, a flexural stiffener 2231 may be incorporated in the device body. Alternatively a flexural stiffener may be comprised in along some longitudinal cross section of the device body. Such stiffeners in some embodiments will be sandwiched between a proximal and distal surface layer of a device body. Mitral assist device 2200 is comprised of device body 2202 and device strap 2211 with anchor elements 2238 deployed by anchor drive 2225. After helical anchoring screws 2239 are affixed into the myocardial tissue, guide sheath 2232 and guide lock 2233 are removed allowing the retrieval of anchor element drive 2225.

FIGS. 23A and 23B show a cross section of screw anchor system 2342 comprising screw anchor element 2334, screw anchor guide elements 2333 and 2332, and screw anchor drive 2335. FIG. 23A shows screw anchor drive 2335 positioned at, but not engaged with, anchor drive slot 2338, and FIG. 23B shows the drive element engaged with the drive slot. A guide system comprised of guide element lock 2333 and guide element sheath 2332 facilitate alignment and engagement of the drive to the drive slot. These guide elements run through screw drive anchor 2335 along a lumen traversing the length of the drive element and are removed from the assembly after deploying the anchoring element by removing guide lock 2333 which in turn releases guide sheath 2332 allowing the guide and drive elements to be removed from the anchoring element. FIGS. 23C and 23D illustrate the delivery and operational configurations of screw anchor element 2334 respectively, where helical screw element 2339 is deployed using screw anchor drive 2335 as described above in FIGS. 23A and 23B.

FIG. 24 represents one embodiment of a steerable delivery catheter for coupling elements. Steering is accomplished by a pulling on steering wire 2441 which causes catheter 2425 to bend. Alternate catheter steering systems known to the art may also be employed.

FIGS. 25 through 27 depict the delivery of a leaflet assist device as described herein using three different approaches. FIG. 25 shows a steerable delivery catheter delivering a device to a target area via an endovascular transseptal approach delivered from the inferior vena cava. As shown the distal end of delivery catheter 2513 has been passed through the septum between the right and left atria. After which the mitral assist device was delivered from the delivery catheter and then oriented such that the mitral assist device body is positioned over the posterior mitral leaflet 2503 and between the anterior and posterior mitral leaflets. The device strap 2511 aligned with the annulus fibrous sinister at the perimeter of the posterior mitral leaflet 2504. The screw anchor system 2542 is then used to affix the mitral assist device in place. The delivery catheter 2513 as depicted in FIG. 25 is a steerable catheter as is known in the art. FIG. 26 depicts an endovascular arterial delivery approach, and FIG. 27 depicts a transapical approach.

FIG. 28 illustrates a mitral assist device in which a flexible stiffening element 2831 has been comprised in the perimeter of the mitral assist device body 2802 to minimize the upward displacement of the mitral assist device during mitral closure. The device body 2802 is comprised of a fabric, polymer sheet, or tissue, the stiffening mechanism may be sewn in place as shown. In some cases a biasing material may be employed to cover the stiffening element. The stiffening element may be comprised of a polymer material, a super elastic material, or a combination of such materials.

What is claimed is:

1. A prosthetic valve coaptation assist device for assisting coaptation of a cardiac valve, the prothetic valve coaptation assist device comprising:
   only one valve assist leaflet; and
   an anchor configured to be attached to a valve annulus,
   wherein the valve assist leaflet is configured to lie over a superior surface of a first valve leaflet when the anchor is attached to the valve annulus, the valve assist leaflet having a fixed end, a ventricular end opposite the fixed end, and first and second curved lateral edges, which face in generally opposite directions from each other and extend between the ventricular and the fixed ends, wherein the valve assist leaflet is coupled to the anchor only at the fixed end of the valve assist leaflet,
   wherein the prosthetic valve coaptation assist device is configured such that when the anchor is attached to the valve annulus, (a) a first open space is formed between the ventricular end of the valve assist leaflet and the valve annulus opposite a first side of the anchor, the first open space accommodating movement of a second valve leaflet in response to blood flow through the cardiac valve, and (b) second and third open spaces are formed in a radial direction between the valve annulus and the first and the second curved lateral edges, respectively,
   wherein the valve assist leaflet is sufficiently flexible and the ventricular end of the valve assist leaflet is freely moveable such that the valve assist leaflet will move in unison with the first valve leaflet and will coapt with the second valve leaflet in response to the blood flow through the cardiac valve.

2. A prosthetic valve coaptation assist device as in claim 1, wherein the ventricular end is entirely convex.

3. A prosthetic valve coaptation assist device for assisting coaptation of cardiac valve, the prosthetic valve coaptation assist device comprising:
   only one valve assist leaflet; and
   an anchor configured to be attached to a native valve annulus,
   wherein the valve assist leaflet is configured to lie over a superior surface of a first native valve leaflet when the anchor is attached to the native valve annulus, the valve assist leaflet having a fixed end, a ventricular end opposite the fixed end, and first and second curved lateral edges, which face in generally opposite directions from each other and extend between the ventricular and the fixed ends, wherein the valve assist leaflet is coupled to the anchor only at the fixed end of the valve assist leaflet,
   wherein the prosthetic valve coaptation assist device is configured such that when the anchor is attached to the native valve annulus, (a) a first open space is formed between the ventricular end of the valve assist leaflet and the native valve annulus opposite a first side of the anchor, the first open space accommodating movement of a second native valve leaflet in response to blood flow through the cardiac valve, and (b) second and third open spaces are formed in a radial direction between the native valve annulus and the first and the second curved lateral edges, respectively,
   wherein the valve assist leaflet is sufficiently flexible and the ventricular end of the valve assist leaflet is freely moveable such that the valve assist leaflet will move in unison with the first native valve leaflet and will coapt with the second native valve leaflet in response to the blood flow through the cardiac valve.

4. A prosthetic valve coaptation assist device as in claim 3, wherein the anchor is configured to be sutured to the native valve annulus.

5. A prosthetic valve coaptation assist device as in claim 3, wherein the valve assist leaflet comprises a body formed from tissue or a synthetic polymer and further comprises a reinforcement structure.

6. A prosthetic valve coaptation assist device as in claim 5, wherein the reinforcement structure comprises a metal reinforcement structure.

7. A prosthetic valve coaptation assist device as in claim 3, wherein the anchor is configured to be attached to a mitral valve or an aortic valve.

8. A prosthetic valve coaptation assist device as in claim 3, wherein the prosthetic valve coaptation assist device is configured to be implanted in an open surgical procedure.

9. A prosthetic valve coaptation assist device as in claim 3, wherein the prosthetic valve coaptation assist device is configured to be advanced endovascularly.

10. A prosthetic valve coaptation assist device as in claim 3, wherein the prosthetic valve coaptation assist device is configured to be advanced transseptally.

11. A prosthetic valve coaptation assist device as in claim 3, wherein the prosthetic valve coaptation assist device is configured to be advanced transapically.

12. A prosthetic valve coaptation assist device as in claim 3, wherein the anchor is configured to self-expand to attach to the native valve annulus.

13. A prosthetic valve coaptation assist device as in claim 12, wherein the anchor includes one or more barbs which penetrate the native valve annulus as the anchor expands.

14. A prosthetic valve coaptation assist device as in claim 3, wherein the only one valve assist leaflet defines an atrioventricular-oriented axis between the fixed and the ventricular ends, and has:
- a first width at the fixed end and a first location along the atrioventricular-oriented axis,
- a second width at a second location along the atrioventricular-oriented axis between the fixed and ventricular ends greater than the first width, and
- a third width less than the second width at a third location along the atrioventricular-oriented axis, the third location being between the second location and the ventricular end along the atrioventricular-oriented axis.

15. A prosthetic valve coaptation assist device as in claim 3, wherein a length of the only one valve assist leaflet in an atrioventricular direction is greater than a greatest width of the only one valve assist leaflet.

16. A prosthetic valve coaptation assist device as in claim 3, wherein the anchor is configured to fully circumscribe the native valve annulus.

17. A prosthetic valve coaptation assist device as in claim 3, wherein the anchor comprises a ring.

18. A prosthetic valve coaptation assist device as in claim 3, wherein the ventricular end is entirely convex.

19. A prosthetic valve coaptation assist device as in claim 3, wherein the only one valve assist leaflet defines an atrioventricular-oriented axis between the fixed and the ventricular ends, and has:
- a first width at the fixed end and a first location along the atrioventricular-oriented axis,
- a second width at a second location along the atrioventricular-oriented axis between the fixed and the ventricular ends less than the first width, and
- a third width greater than the second width at a third location along the atrioventricular-oriented axis, the third location being between the second location and the ventricular end along the atrioventricular-oriented axis.

20. A prosthetic valve coaptation assist device as in claim 19, wherein the only one valve assist leaflet has a fourth width less than the third width at a fourth location along the atrioventricular-oriented axis, the fourth location being between the third location and the ventricular end along the atrioventricular-oriented axis.

21. A prosthetic valve coaptation assist device as in claim 19, wherein the ventricular end is entirely convex.

22. A prosthetic valve coaptation assist device as in claim 3, wherein the first and the second curved lateral edges are shaped so as to define respective first and second concave portions.

23. A prosthetic valve coaptation assist device as in claim 3, wherein a length of the anchor is greater than a greatest length of the valve assist leaflet in an atrioventricular direction.

24. A prosthetic valve coaptation assist device for assisting coaptation of a cardiac valve, the prosthetic valve coaptation assist device comprising:
- only one valve assist leaflet; and
- an anchor configured to be attached to a native valve annulus,
- wherein the valve assist leaflet is configured to lie over a superior surface of a first native valve leaflet when the anchor is attached to the native valve annulus, the valve assist leaflet having a fixed end coupled to a first side of the anchor and a ventricular end opposite the fixed end,
- wherein the prosthetic valve coaptation assist device is configured such that when the anchor is attached to the native valve annulus, an open space is formed between the ventricular end of the valve assist leaflet and the native valve annulus opposite the first side of the anchor, the open space accommodating movement of a second native valve leaflet in response to blood flow through the cardiac valve,
- wherein the valve assist leaflet is sufficiently flexible and the ventricular end of the valve assist leaflet is freely moveable such that the valve assist leaflet will move in unison with the first native valve leaflet and will coapt with the second native valve leaflet in response to the blood flow through the cardiac valve, and
- wherein a length of the valve assist leaflet in an atrioventricular direction is greater than a greatest width of the valve assist leaflet.

* * * * *